(12) United States Patent
Alexander et al.

(10) Patent No.: US 10,390,813 B2
(45) Date of Patent: Aug. 27, 2019

(54) SYSTEMS, IMPLANTS, TOOLS, AND METHODS FOR TREATMENTS OF PELVIC CONDITIONS

(71) Applicant: Boston Scientific Scimed, Inc., Maple Grove, MN (US)

(72) Inventors: James A. Alexander, Excelsior, MN (US); John R. Frigstad, St. Anthony, MN (US); Carrie L. Herman, Mayer, MN (US); Justin H. Huelman, Lino Lakes, MN (US); Karl A. Jagger, Deephaven, MN (US); Chaouki A. Khamis, Edina, MN (US); Michael A. Knipfer, Maple Grove, MN (US); Jeffrey M. O'Hern, Golden Valley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 305 days.

(21) Appl. No.: 14/573,859

(22) Filed: Dec. 17, 2014

(65) Prior Publication Data

US 2015/0105623 A1    Apr. 16, 2015

Related U.S. Application Data

(63) Continuation of application No. 13/566,756, filed on Aug. 3, 2012, now abandoned.
(Continued)

(51) Int. Cl.
*A61B 17/02* (2006.01)
*A61B 1/00* (2006.01)
(Continued)

(52) U.S. Cl.
CPC ...... *A61B 17/0218* (2013.01); *A61B 1/00165* (2013.01); *A61B 1/32* (2013.01);
(Continued)

(58) Field of Classification Search
CPC . A61B 17/02; A61B 17/0206; A61B 17/0218; A61B 17/3439; A61B 17/3462;
(Continued)

(56) References Cited

U.S. PATENT DOCUMENTS 2,738,790 A  3/1956  Todt et al.
3,124,136 A  3/1964  Usher
(Continued)

FOREIGN PATENT DOCUMENTS

AU  2002241673  11/2005
CA  2404459  8/2005
(Continued)

OTHER PUBLICATIONS

"We're staying ahead of the curve" Introducing the IVS Tunneller Device for Tension Free Procedures, Tyco Healthcare, 3 pages (2002).
(Continued)

*Primary Examiner* — Eric S Gibson
(74) *Attorney, Agent, or Firm* — Brake Hughes Bellermann LLP

(57) ABSTRACT

Described are various embodiments of surgical procedure systems, devices, tools, and methods, useful for treating pelvic conditions such as vaginal prolapse and other conditions caused by muscle and ligament weakness, the devices and tools being useful for accessing a posterior region of pelvic anatomy, and related methods. Such devices can include retractors, introducers, and other devices for accessing desired areas of a patient's anatomy.

10 Claims, 27 Drawing Sheets

Related U.S. Application Data

(60) Provisional application No. 61/515,685, filed on Aug. 5, 2011.

(51) Int. Cl.
*A61B 1/32* (2006.01)
*A61B 17/00* (2006.01)

(52) U.S. Cl.
CPC .............. A61B 2017/00336 (2013.01); *A61B 2017/00805* (2013.01)

(58) Field of Classification Search
CPC .... A61B 2017/3433; A61B 2017/3441; A61B 2017/3443; A61B 2017/3447; A61B 2017/345; A61B 2017/3452; A61B 2017/3456; A61B 2017/346; A61B 1/32; A61B 1/303; A61B 1/31
See application file for complete search history.

(56) References Cited

U.S. PATENT DOCUMENTS

| | | |
|---|---|---|
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,815,576 A | 6/1974 | Balaban |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,235,238 A | 11/1980 | Ogiu et al. |
| 4,246,660 A | 1/1981 | Wevers |
| 4,432,351 A * | 2/1984 | Hoary ............... A61B 1/32 600/220 |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,690,132 A * | 9/1987 | Bayer ............... A61B 1/32 600/184 |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,932,962 A | 6/1990 | Yoon et al. |
| 4,938,760 A | 7/1990 | Burton et al. |
| 4,969,892 A | 11/1990 | Burton et al. |
| 5,007,894 A | 4/1991 | Enhorning |
| 5,012,822 A | 5/1991 | Schwarz |
| 5,013,292 A | 5/1991 | Lemay |
| 5,013,316 A | 5/1991 | Goble et al. |
| 5,019,032 A | 5/1991 | Robertson |
| 5,032,508 A | 7/1991 | Naughton et al. |
| 5,036,867 A | 8/1991 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,141,520 A | 8/1992 | Goble et al. |
| 5,149,329 A | 9/1992 | Richardson |
| 5,188,636 A | 2/1993 | Fedotov |
| 5,209,756 A | 5/1993 | Seedhom et al. |
| 5,250,033 A | 10/1993 | Evans et al. |
| 5,256,133 A | 10/1993 | Spitz |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,345,927 A * | 9/1994 | Bonutti ............. A61B 17/0218 600/204 |
| 5,362,294 A | 11/1994 | Seitzinger |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,474,518 A | 12/1995 | Velaquez |
| 5,474,543 A | 12/1995 | McKay |
| 5,518,504 A | 5/1996 | Polyak |
| 5,520,700 A | 5/1996 | Beyer et al. |
| 5,520,703 A | 5/1996 | Essig |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,633,286 A | 5/1997 | Chen |
| 5,643,320 A | 7/1997 | Lower et al. |
| 5,669,935 A | 9/1997 | Rosenman et al. |
| 5,683,349 A | 11/1997 | Makower et al. |
| 5,697,931 A | 12/1997 | Thompson |
| 5,709,708 A | 1/1998 | Thal |
| 5,725,541 A | 3/1998 | Anspach, III et al. |
| 5,741,282 A | 4/1998 | Anspach, III et al. |
| 5,782,916 A | 7/1998 | Pintauro et al. |
| 5,785,640 A | 7/1998 | Kresch et al. |
| 5,807,403 A | 9/1998 | Boyar et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,922,026 A | 7/1999 | Chin |
| 5,925,047 A | 7/1999 | Errico et al. |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,010,447 A | 1/2000 | Kardjian |
| 6,027,523 A | 2/2000 | Schmieding |
| 6,030,393 A | 2/2000 | Corlew |
| 6,031,148 A | 2/2000 | Hayes et al. |
| 6,036,701 A | 3/2000 | Rosenman |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,099,538 A | 8/2000 | Moses |
| 6,099,551 A | 8/2000 | Gabbay |
| 6,099,552 A | 8/2000 | Adams |
| 6,106,545 A | 8/2000 | Egan |
| 6,110,101 A | 8/2000 | Tihon et al. |

(56) References Cited

U.S. PATENT DOCUMENTS

| | | |
|---|---|---|
| 6,117,067 A | 9/2000 | Gil-Vernet |
| 6,127,597 A | 10/2000 | Beyer et al. |
| 6,168,611 B1 | 1/2001 | Risvi |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,264,676 B1 | 7/2001 | Gellman et al. |
| 6,273,852 B1 | 8/2001 | Lehe et al. |
| 6,302,840 B1 | 10/2001 | Benderev |
| 6,306,079 B1 | 10/2001 | Trabucco |
| 6,322,492 B1 | 11/2001 | Kovac |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van der Burg et al. |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,414,179 B1 | 7/2002 | Banville |
| 6,423,080 B1 | 7/2002 | Gellman et al. |
| 6,451,024 B1 | 9/2002 | Thompson et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,491,703 B1 | 12/2002 | Ulmsten |
| 6,494,906 B1 | 12/2002 | Owens |
| 6,502,578 B2 | 1/2003 | Raz et al. |
| 6,506,190 B1 | 1/2003 | Walshe |
| 6,530,943 B1 | 3/2003 | Hoepffner et al. |
| 6,575,897 B1 | 6/2003 | Ory |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman et al. |
| 6,691,711 B2 | 2/2004 | Raz |
| 6,699,175 B2 | 3/2004 | Miller |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,830,052 B2 | 12/2004 | Carter et al. |
| 6,881,184 B2 | 4/2005 | Zappala |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,953,428 B2 | 10/2005 | Gellman et al. |
| 6,960,160 B2 | 11/2005 | Browning |
| 6,971,986 B2 | 12/2005 | Staskin et al. |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,065 B2 | 8/2006 | Ulmsten et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jaquetin |
| 7,175,591 B2 | 2/2007 | Kaladelfos |
| 7,198,597 B2 | 4/2007 | Siegel et al. |
| 7,226,407 B2 | 6/2007 | Kammerer |
| 7,226,408 B2 | 6/2007 | Hared et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,297,102 B2 | 11/2007 | Smith et al. |
| 7,299,803 B2 | 11/2007 | Kovac |
| 7,303,525 B2 | 12/2007 | Watschke et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Amal |
| 7,431,690 B2 | 10/2008 | Bryon et al. |
| 7,491,168 B2 * | 2/2009 | Raymond .............. A61B 17/02 600/231 |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,686,759 B2 | 3/2010 | Sater |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,766,926 B2 | 8/2010 | Bosely et al. |
| 7,789,821 B2 | 9/2010 | Browning |
| 7,981,024 B2 | 7/2011 | Levy |
| 8,172,745 B2 | 5/2012 | Rosenblatt |
| 2001/0049467 A1 | 12/2001 | Lehe et al. |
| 2002/0007222 A1 | 1/2002 | Desai |
| 2002/0028980 A1 | 3/2002 | Thierfelder et al. |
| 2002/0128670 A1 | 9/2002 | Ulmsten et al. |
| 2002/0147382 A1 | 10/2002 | Neisz et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0036676 A1 | 2/2003 | Scetbon |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0225181 A1 | 11/2004 | Chu et al. |
| 2004/0267088 A1 | 12/2004 | Kammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0038451 A1 | 2/2005 | Rao et al. |
| 2005/0055104 A1 | 3/2005 | Arnal et al. |
| 2005/0131391 A1 | 6/2005 | Chu et al. |
| 2005/0131393 A1 | 6/2005 | Chu et al. |

(56) References Cited

U.S. PATENT DOCUMENTS

| | | |
|---|---|---|
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0015010 A1 | 1/2006 | Jaffe et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac |
| 2006/0028828 A1 | 7/2006 | Cox et al. |
| 2006/0173237 A1 | 8/2006 | Jacquetin |
| 2006/0195007 A1 | 8/2006 | Anderson |
| 2006/0195011 A1 | 8/2006 | Arnal |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0287571 A1 | 12/2006 | Gozzi |
| 2007/0015953 A1 | 1/2007 | MacLean |
| 2007/0038216 A1* | 2/2007 | Hamada ............... A61B 17/02 606/53 |
| 2007/0078295 A1 | 4/2007 | Iandgrebe |
| 2007/0173864 A1 | 7/2007 | Chu |
| 2008/0039678 A1 | 2/2008 | Montpetit et al. |
| 2008/0140218 A1 | 6/2008 | Staskin et al. |
| 2008/0207988 A1 | 8/2008 | Hanes |
| 2008/0214898 A1 | 9/2008 | Warren |
| 2008/0300607 A1 | 12/2008 | Meade et al. |
| 2009/0005634 A1 | 1/2009 | Rane |
| 2009/0012353 A1 | 1/2009 | Beyer |
| 2009/0221868 A1 | 9/2009 | Evans |
| 2010/0022822 A1 | 1/2010 | Walshe |
| 2010/0179575 A1 | 7/2010 | Von Pechmann et al. |
| 2010/0261950 A1 | 10/2010 | Lund |
| 2010/0280627 A1 | 11/2010 | Hanes, II |
| 2011/0124954 A1 | 5/2011 | Odahl |
| 2011/0174313 A1 | 7/2011 | Von Pechmann et al. |
| 2012/0016185 A1 | 1/2012 | Sherts et al. |

FOREIGN PATENT DOCUMENTS

| | | |
|---|---|---|
| DE | 2305815 | 2/1973 |
| DE | 4220283 C2 | 5/1994 |
| DE | 19544162 | 4/1997 |
| DE | 10211360 | 9/2003 |
| DE | 20016866 | 3/2007 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 1093758 A1 | 4/2001 |
| EP | 1060714 A3 | 9/2002 |
| EP | 1342450 B1 | 9/2003 |
| FR | 2787990 A1 | 7/2000 |
| FR | 2852813 A1 | 1/2004 |
| GB | 2268690 A | 1/1994 |
| GB | 2353220 A | 10/2000 |
| IT | 1299162 | 4/1998 |
| SU | 1225547 A1 | 4/1986 |
| SU | 1342486 A | 10/1987 |
| WO | WO9317635 A1 | 9/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO1999/059477 | 11/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0040158 A2 | 7/2000 |
| WO | WO0057812 A1 | 10/2000 |
| WO | WO0066030 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO0145588 A1 | 6/2001 |
| WO | WO0145589 A1 | 6/2001 |
| WO | WO0156499 A1 | 8/2001 |
| WO | WO0228312 A1 | 4/2002 |
| WO | WO0228315 A2 | 4/2002 |
| WO | WO0230293 A1 | 4/2002 |
| WO | WO0232284 A2 | 4/2002 |
| WO | WO0234124 A2 | 5/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO02089704 A2 | 11/2002 |
| WO | WO03017948 A1 | 3/2003 |
| WO | WO0303778 A1 | 4/2003 |
| WO | WO03028585 A2 | 4/2003 |
| WO | WO03037215 A2 | 5/2003 |
| WO | WO03041613 A1 | 5/2003 |
| WO | WO03047435 A1 | 6/2003 |
| WO | WO03068107 A1 | 8/2003 |
| WO | WO03075792 A1 | 9/2003 |
| WO | WO03092546 A2 | 11/2003 |
| WO | WO03096929 A1 | 11/2003 |
| WO | WO2004012626 A1 | 2/2004 |
| WO | WO2004016196 A2 | 2/2004 |
| WO | WO2004/017862 | 3/2004 |
| WO | WO2004017862 A2 | 3/2004 |
| WO | WO2004034912 A1 | 4/2004 |
| WO | WO2005037132 A2 | 4/2005 |
| WO | WO2005079702 A1 | 9/2005 |
| WO | WO2005122954 A1 | 12/2005 |
| WO | WO2006015031 A2 | 2/2006 |
| WO | WO2006108145 A1 | 10/2006 |
| WO | WO2007011341 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |
| WO | WO2011/082350 | 7/2011 |

OTHER PUBLICATIONS

Advantage A/T™, Surgical Mesh Sling Kit, Boston Scientific, 6 pages (2002).

(56) References Cited

OTHER PUBLICATIONS

Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).
Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).
Araki, Tohru et al., The Loop-Loosening Procedure for Urination Difficulties After Stamey Suspension of the Vesical Neck, The Journal of Urology, vol. 144, pp. 319-323 (Aug. 1990).
Asmussen, M. et.al., Simultaneous Urethro-Cystometry With a New Technique, Scand J Urol Nephrol 10, p. 7-11 (1976).
Beck, Peter R. et al., Treatment of Urinary Stress Incontinence With Anterior Colporrhaphy, Obstetrics and Gynecology, vol. 59 (No. 3), pp. 269-274 (Mar. 1982).
Benderev, Theodore V., MD, A Modified Percutaneous Outpatient Bladder Neck Suspension System, Journal of Urology, vol. 152, pp. 2316-2320 (Dec. 1994).
Benderev, Theodore V., MD, Anchor Fixation and Other Modifications of Endoscopic Bladder Neck Suspension, Urology, vol. 40, No. 5, pp. 409-418 (Nov. 1992).
Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995).
Blaivas, Jerry et al., Pubovaginal Fascial Sling for the Treatment of Complicated Stress Urinary Incontinence, The Journal of Urology, vol. 145, pp. 1214-1218 (Jun. 1991).
Blaivas, Jerry et al., Type III Stress Urinary Incontinence: Importance of Proper Diagnosis and Treatment, Surgical Forum, pp. 473-475, (1984).
Blaivas, Jerry, Commentary: Pubovaginal Sling Procedure, Experience with Pubovaginal Slings, pp. 93-101 (1990).
Boyles, Sarah Hamilton et al., Procedures for Urinary Incontinence in the United States, 1979-1997, Am J Obstet Gynecol, vol. 189, n. 1, pp. 70-75 (Jul. 2003).
Bryans, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292-294 (Feb. 1979).
Burch, John C., Urethrovaginal Fixation to Cooper's Ligament for Correction of Stress Incontinence, Cystocele, and Prolapse, Am. J. Obst. & Gyn, vol. 31, pp. 281-290 (1961).
Capio™ CL—Transvaginal Suture Capturing Device—Transvaginal Suture Fixation to Coopers Ligament for Sling Procedures, Boston Scientific, Microvasivel, 8 pages, (2002).
Cervigni, Mauro et al., The Use of Synthetics in the Treatment of Pelvic Organ Prolapse, Voiding Dysfunction and Female Urology, vol. 11, pp. 429-435 (2001).
Choe, Jong M. et al., Gore-Tex Patch Sling: 7 Years Later, Urology, vol. 54, pp. 641-646 (1999).
Cook/Ob Gyn®, Urogynecology, Copyright Cook Urological Inc., pp. 1-36 (1996).
Dargent, D. et al., Insertion of a Suburethral Sling Through the Obturator Membrane in the Treatment of Female Urinary Incontinence, Gynecol Obstet Fertil, vol. 30, pp. 576-582 (2002).
Das, Sakti et al., Laparoscopic Colpo-Suspension, The Journal of Urology, vol. 154, pp. 1119-1121 (Sep. 1995).
Debodinance, Philipp et al., "Tolerance of Synthetic Tissues in Touch With Vaginal Scars: Review to the Point of 287 Cases", European Journal of Obstetrics & Gynecology and Reproductive Biology 87 (1999) pp. 23-30.
Decter, Ross M., Use of the Fascial Sling for Neurogenic Incontinence: Lessons Learned, The Journal of Urology, vol. 150, pp. 683-686 (Aug. 1993).
Delancey, John, MD, Structural Support of the Urethra as it Relates to Stress Urinary Incontinence: The Hammock Hypothesis, Am J Obstet Gynecol, vol. 170 No. 6, pp. 1713-1723 (Jun. 1994).

Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.
Diana, et al., Treatment of Vaginal Vault Prolapse With Abdominal Sacral Colpopexy Using Prolene Mesh, American Journal of Surgery, vol. 179, pp. 126-128, (Feb. 2000).
Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).
Enzelsberger, H. et al., Urodynamic and Radiologic Parameters Before and After Loop Surgery for Recurrent Urinary Stress Incontinence, Acta Obstet Gynecol Scand, 69, pp. 51-54 (1990).
Eriksen, Bjarne C. et al., Long-Term Effectiveness of the Burch Colposuspension in Female Urinary Stress Incontinence, Acta Obstet Gynecol Scand, 69, pp. 45-50 (1990).
Falconer, C. et al., Clinical Outcome and Changes in Connective Tissue Metabolism After Intravaginal Slingplasty in Stress Incontinence Women, International Urogynecology Journal, pp. 133-137 (1966).
Falconer, C. et al., Influence of Different Sling Materials of Connective Tissue Metabolism in Stress Urinary Incontinent Women, International Urogynecology Journal, Supp. 2, pp. S19-S23 (2001).
Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).
Farquhar, Cynthia M. et al., Hysterectomy Rates in the United States 1990-1997, Obstetrics & Gynecology, vol. 99, n. 2, pp. 229-234 (Feb. 2002).
Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).
Flood, C.G. et al., Anterior Colporrhaphy Reinforce With Marlex Mesh for the Treatment of Cystoceles, International Urogynecology Journal, vol. 9, pp. 200-204 (1998).
Gilja, Ivan et al., A Modified Raz Bladder Neck Suspension Operation (Transvaginal Burch), The Journal of Urology, vol. 153, pp. 1455-1457 (May 1995).
Gittes, Ruben F. et al., No-Incision Pubovaginal Suspension for Stress Incontinence, The Journal of Urology, vol. 138 (Sep. 1987).
Guner, et al., Transvaginal Sacrospinous Colpopexy for Marked Uterovaginal and Vault Prolapse, Inter J of Gynec & Obstetrics, vol. 74, pp. 165-170 (2001).
Gynecare TVT Tension-Free Support for Incontinence, The tension-free solution to female Incontinence, Gynecare Worldwide,6 pages, (2002).
Handa, Victoria L. et al, Banked Human Fascia Lata for the Suburethral Sling Procedure: A Preliminary Report, Obstetrics & Gynecology, vol. 88 No. 6, 5 pages (Dec. 1996).
Heit, Michael et al., Predicting Treatment Choice for Patients With Pelvic Organ Prolapse, Obstetrics & Gynecology, vol. 101. n. 6, pp. 1279-1284 (Jun. 2003).
Henriksson, L. et al., A Urodynamic Evaluation of the Effects of Abdominal Urethrocystopexy and Vaginal Sling Urethroplasty in Women With Stress Incontinence, Am. J. Obstet. Gynecol. vol. 131, No. 1, pp. 77-82 (Mar. 1, 1978).
Hodgkinson, C. Paul et.al., Urinary Stress Incontinence in the Female, Department of Gynecology and Obstetrics, Henry Ford Hospital, vol. 10, No. 5, p. 493-499, (Nov. 1957).
Holschneider, C. H., et al., The Modified Pereyra Procedure in Recurrent Stress Urinary Incontinence: A 15-year Review, Obstetrics & Gynecology, vol. 83, No. 4, pp. 573-578 (Apr. 1994).
Horbach, Nicollette S., et al., Instruments and Methods, A Suburethral Sling Procedure with Polytetratluoroethylene for the Treatment of Genuine Stress Incontinence in Patients with Low Urethral Closure Pressure, Obstetrics & Gynecology, vol. 71, No. 4, pp. 648-652 (Apr. 1998).
Ingelman-Sunberg, A. et al., Surgical Treatment of Female Urinary Stress Incontinence, Contr. Gynec. Obstet., vol. 10, pp. 51-69 (1983).
IVS Tunneller—A Universal instrument for anterior and posterior intra-vaginal tape placement, Tyco Healthcare, 4 pages (Aug. 2002).

(56) References Cited

OTHER PUBLICATIONS

IVS Tunneller—ein universelles Instrument fur die Intra Vaginal Schlingenplastik, Tyco Healthcare, 4 pages (2001).
Jeffcoate, T.N.A. et al., The Results of the Aldridge Sling Operation for Stress Incontinence, Journal of Obstetrics and Gynaecology, pp. 36-39 (1956).
Jones, N.H.J. Reay et al., Pelvic Connective Tissue Resilience Decreases With Vaginal Delivery, Menopause and Uterine Prolapse, Br J Surg, vol. 90, n. 4, pp. 466-472 (Apr. 2003).
Julian, Thomas, The Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).
Karram, Mickey et al., Patch Procedure: Modified Transvaginal Fascia Lata Sling for Recurrent for Severe Stress Urinary Incontinence, vol. 75, pp. 461-463 (Mar. 1990).
Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).
Kersey, J., The Gauze Hammock Sling Operation in the Treatment of Stress Incontintence, British Journal of Obstetrics and Gynaecology, vol. 90, pp. 945-949 (Oct. 1983).
Klutke, Carl et al., The Anatomy of Stress Incontinence: Magentic Resonance Imaging of the Female Bladder Neck and Urethra, The Journal of Urology, vol. 143, pp. 563-566 (Mar. 1990).
Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).
Klutke, John M.D. et al, The promise of tension-free vaginal tape for female SUI, Contemporary Urology, 7 pages (Oct. 2000).
Korda, A. et al., Experience With Silastic Slings for Female Urinary Incontience, Aust NZ J. Obstet Gynaecol, vol. 29, pp. 150-154 (May 1989).
Kovac, S. Robert, et al, Pubic Bone Suburethral Stabilization Sling for Recurrent Urinary Incontinence, Obstetrics & Gynecoloy, vol. 89, No. 4, pp. 624-627 (Apr. 1997).
Kovac, S. Robert, et al, Pubic Bone Suburethral Stabilization Sling: A Long Term Cure for SUI?, Contemporary OB/GYN, 10 pages (Feb. 1998).
Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).
Kovac, Stephen Robert, M.D., Cirriculum Vitae, pp. 1-33 (Jun. 18, 1999).
Leach, Gary E., et al., Female Stress Urinary Incontinence Clinical Guidelines Panel Report on Surgical Management of Female Stress Urinary Incontinence, American Urological Association, vol. 158, pp. 875-880 (Sep. 1997).
Leach, Gary E., MD, Bone Fixation Technique for Transvaginal Needle Suspension, Urology vol. XXXI, No. 5, pp. 388-390 (May 1988).
Lichtenstein, Irving L. et al, The Tension Free Hernioplasty, The American Journal of Surgery, vol. 157 pp. 188-193 (Feb. 1989).
Loughlin, Kevin R. et al., Review of an 8-Year Experience With Modifications of Endoscopic Suspension of the Bladder Neck for Female Stress Incontinence, The Journal of Uroloyg, vol. 143, pp. 44-45 (1990).
Luber, Karl M. et al., The Demographics of Pelvic Floor Disorders; Current Observations and Future Projections, Am J Obstet Gynecol, vol. 184, n. 7, pp. 1496-1503 (Jun. 2001).
Mage, Technique Chirurgicale, L'Interpostion D'Un Treillis Synthetique Dans La Cure Par Vole Vaginale Des Prolapsus Genitaux, J Gynecol Obstet Biol Reprod, vol. 28, pp. 825-829 (1999).
Marchionni, Mauro et al., True Incidence of Vaginal Vault Prolapse— Thirteen Years of Experience, Journal of Reproductive Medicine, vol. 44, n. 8, pp. 679-684 (Aug. 199).
Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).

Marshall, Victor Fray et al. The Correction of Stress Incontinence by Simple Vesicourethral Suspension, Surgery, Gynecology and Obstetrics, vol. 88, pp. 509-518 (1949).
McGuire, Edward J. et al., Pubovaginal Sling Procedure for Stress Incontinence, The Journal of Urology, vol. 119, pp. 82-84 (Jan. 1978).
McGuire, Edward J. et al., Abdominal Procedures for Stress Incontinence, Urologic Clinics of North America, pp. 285-290, vol. 12, No. 2 (May 1985).
McGuire, Edward J. et al., Experience With Pubovaginal Slings for Urinary Incontinence at The University of Michigan, Journal of Urology, vol. 138, pp. 90-93(1987).
McGuire, Edwared J. et al., Abdominal Fascial Slings, Slings, Raz Female Urology, p. 369-375 (1996).
McGuire™ Suture Buide, The McGuire™ Suture Guide, a single use instrument designed for the placement of a suburethral sling, Bard, 2 pages (2001).
McIndoe, G. A. et al., The Aldridge Sling Procedure in the Treatment of Urinary Stress Incontinence, Aust. N Z Journal of Obstet Gynecology, pp. 238-239 (Aug. 1987).
McKiel, Charles F. Jr., et al, Marshall-Marchetti Procedure Modification, vol. 96, pp. 737-739 (Nov. 1966).
Migliari, Roberto et al., Tension-Free Vaginal Mesh Repair for Anterior Vaginal Wall Prolapse, Eur Urol, vol. 38, pp. 151-155 (Oct. 1999).
Migliari, Roberto et al., Treatment Results Using a Mixed Fiber Mesh in Patients With Grade IV Cystocele, Journal of Urology, vol. 161, pp. 1255-1258 (Apr. 1999).
Moir, J, Chassar et.al., The Gauze-Hammock Operation, The Journal of Obstetrics and Gynaecology of British Commonwealth, vol. 75 No. 1, pp. 1-9 (Jan. 1968).
Morgan, J. E., A Sling Operation, Using Marlex Polypropylene Mesh, for the Treatment of Recurrent Stress Incontinence, Am. J. Obst. & Gynecol, pp. 369-377 (Feb. 1970).
Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).
Morley, George W. et al., Sacrospinous Ligament Fixations for Eversion of the Vagina, Am J Obstet Gyn, vol. 158, n. 4, pp. 872-881 (Apr. 1988).
Narik, G. et.al., A Simplified Sling Operation Suitable for Routine Use, Gynecological and Obstetrical Clinic, University of Vienna, vol. 84, No. 3, p. 400-405, (Aug. 1, 1962).
Natale, F. et al., Tension Free Cystocele Repair (TCR): Long-Term Follow-Up, International Urogyinecoioay Journal, vol. 11, supp. 1, p. 851 (Oct. 2000).
Nichols, David H., The Mersilene Mesh Gauze-Hammock for Severe Urinary Stress Incontinence, Obstetrics and Gynecology, vol. 41, pp. 88-93 (Jan. 1973).
Nicita, Giulio, A New Operation for Genitourinary Prolapse, Journal of Urology, vol. 160, pp. 741-745 (Sep. 1998).
Niknejad, Kathleen et al., Autologous and Synthetic Urethral Slings for Female Incontinence, Urol Clin N Am, vol. 29, pp. 597-611 (2002).
Norris, Jeffrey P. et al., Use of Synthetic Material in Sling Surgery: A Minimally Invasive Approach, Journal of Endourology, vol. 10, pp. 227-230 (Jun. 1996).
O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).
Ostergard, Donald R. et al., Urogynecology and Urodynamics Theory and Practice, pp. 569-579 (1996).
Paraiso et al., Laparoscopic Surgery for Enterocele, Vaginal Apex Prolapse and Rectocele, Int. Urogynecol J, vol. 10, pp. 223-229 (1999).
Parra, R. O., et al, Experience With a Simplified Technique for the Treatment of Female Stress Urinary Incontinence, British Journal of Urology, pp. 615-617 (1990).
Pelosi, Marco Antonio III et al., Pubic Bone Suburethral Stabilization Sling: Laparoscopic Assessment of a Transvaginal Operation

(56) References Cited

OTHER PUBLICATIONS for the Treatment of Stress Urinary Incontinence, Journal of Laparoendoscopic & Advaned Surgical Techniques, vol. 9, No. 1 pp. 45-50 (1999).

Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).

Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).

Peter E. Papa Petros et al., Cure of Stress Incontinence by Repair of External Anal Sphincter, Acta Obstet Gynecol Scand, vol. 69, Sup 153, p. 75 (1990).

Peter Petros et al., Anchoring the Midurethra Restores Bladder-Neck Anatomy and Continence, The Lancet, vol. 354, pp. 997-998 (Sep. 18, 1999).

Petros, Peter E. Papa et al., An Anatomical Basis for Success and Failure of Female Incontinence Surgery, Scandinavian Journal of Neurourology and Urodynamics, Sup 153, pp. 55-60 (1993).

Petros, Peter E. Papa et al., An Analysis of Rapid Pad Testing and the History for the Diagnosis of Stress Incontinence, Acta Obstet Gynecol Scand; vol. 71, pp. 529-536 (1992).

Petros, Peter E. Papa et al., An Integral Therory of Female Urinary Incontinence, Acta Obstetricia et Gynecologica Scandinavica, vol. 69 Sup. 153, pp. 7-31 (1990).

Petros, Peter E. Papa et al., Bladder Instability in Women: A Premature Activation of the Micturition Reflex, Scandinavian Journal of Neurourology and Urodynamics, Sup 153, pp. 235-239 (1993).

Petros, Peter E. Papa et al., Cough Transmission Ratio: An Indicator of Suburethral Vaginal Wall Tension Rather Than Urethral Closure, Acta Obstet Gynecol Scand, vol. 69, Sup 153, pp. 37-39 (1990).

Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).

Petros, Peter E. Papa et al., Further Development of the Intravaginal Slingplasty Procedure—IVS III—(With Midline "Tuck"), Scandinavian Journal of Neurourology and Urodynamics, Sup 153, p. 69-71. (1993).

Petros, Peter E. Papa et al., Medium-Term Follow-Up of the Intravaginal Slingplasty Operation Indicates Minimal Deterioration of Urinary Continence With Time, (3 pages) (1999).

Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).

Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).

Petros, Peter E. Papa et al., Part II: The Biomechanics of Vaginal Tissue and Supporting Ligaments With Special Relevance to the Pathogenesis of Female Urinary Incontinence, Scandinavian Journal of Neurourology and Urodynamics, Sup 153, pp. 29-40 plus cover sheet (1993).

Petros, Peter E. Papa et al., Part III: Surgical Principles Deriving From the Theory, Scandinavian Journal of Neurourology and Urodynamics, Sup 153, pp. 41-52 (1993).

Petros, Peter E. Papa et al., Part IV: Surgical Appliations of the Theory—Development of the Intravaginal Sling Pklasty (IVS) Procedure, Scandinavian Journal of Neurourology and Uredynamies, Sup 153, pp. 53-54 (1993).

Petros, Peter E. Papa et al., Pinch Test for Diagnosis of Stress Urinary Incontinence, Acta Obstet Gynecol Scand, vol. 69, Sup 153, pp. 33-35 (1990).

Petros, Peter E. Papa et al., Pregnancy Effects on the Intravaginal Sling Operation, Acta Obstet Gynecol Scand, vol. 69, Sup 153, pp. 77-79 (1990).

Petros, Peter E. Papa et al., The Autogenic Ligament Procedure: A Technique for Planned Formation of an Artificial Neo-Ligament, Acta Obstet Gynecol Scand, vol. 69, Sup 153, pp. 43-51 (1990).

Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup 153, pp. 53-59 (1990).

Petros, Peter E. Papa et al., The Development of the Intravaginal Slingplasty Procedure: IVS II—(With Bilateral "Tucks"), Scandinavian Journal of Neurourology and Urodynamics, Sup 153, pp. 61-67 (1993).

Petros, Peter E. Papa et al., The Free Graft Procedure for Cure of the Tethered Vagina Syndrome, Scandinavian Journal of Neurourology and Urodynamics, Sup 153; pp. 85-87(1993).

Petros, Peter E. Papa et al., The Further Development of the Intravaginal Slingplasty Procedure—IVS IV—(With "Double Breasted" Unattached Vaginal Flap Repair and "Tree" Vaginal Tapes), Scandinavian Journal of Neurourology and Urodynamics, Sup 153, p. 73-75 (1993).

Petros, Peter E. Papa et al., The Further Development of the Intravaginal Slingplasty Procedure—IVS V—(With "Double Breasted" Unattached Vaginal Flap Repair and Permanent Sling)., Scandinavian Journal of Neurourology and Urodynamics, Sup 153, pp. 77-79 (1993).

Petros, Peter E. Papa et al., The Intravaginal Slingplasty Operation, A Minimally Invasive Technique for Cure of Urinary Incontinence in the Female, Aust. NZ J Obstet Gynaecol, vol. 36, n. 4, pp. 453-461 (1996).

Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81-84 (1993).

Petros, Peter E. Papa. et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pp. 89-93 (1993).

Petros, Peter E. Papa et al., The Role of a Lax Posterior Vaginal Fornix in the Causation of Stress and Urgency Symptoms: A Preliminary Report, Acta Obstet Gynecol Scand, vol. 69, Sup 153, pp. 71-73 (1990).

Petros, Peter E. Papa et al., The Tethered Vagina Syndrome, Post Surgical Incontinence and I-Plasty Operation for Cure, Acta Obstet Gynecol Scand, vol. 69, Sup 153, pp. 63-67 (1990).

Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1990).

Petros, Peter E. Papa et al., Urethral Pressure Increase on Effort Originates From Within the Urethra, and Continence From Musculovaginal Closure, Scandinavian Journal of Neurourology and Urodynamics, pp. 337-350 (1995).

Petros, Peter E. Papa, Development of Generic Models for Ambulatory Vaginal Surgery—Preliminary Report,International Urogynecology Journal, pp. 20-27 (1998).

Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270-278, (1997).

Petros, Peter E. Papa, Vault Prolapse II; Restoration of Dynamic Vaginal Supports by Infracoccygeal Sacropexy, an Axial Day-Case Vaginal Procedure, Int Urogynecol J, vol. 12, pp. 296-303 (2001).

Rackley, Raymond R. et al., Tension-Free Vaginal Tape and Percutaneous Vaginal Tape Sling Procedures, Techniques in Urology, vol. 7, No. 2, pp. 90-100 (2001).

Rackley, Raymond R. M.D., Synthetic Slings: Five Steps for Successful Placement, Urology Times, p. 46,48,49 (Jun. 2000).

Raz, Shlomo, et al., The Raz Bladder Neck Suspension Results in 206 Patients, The Journal of Urology, pp. 845-846 (1992).

Raz, Shlomo, Female Urology, pp. 80-86, 369-398, 435-442 (1996).

Raz, Shlomo, MD, Modified Bladder Neck Suspension for Female Stress Incontinence, Urology, vol. XVII, No. 1, pp. 82-85 (Jan. 1981).

Richardson, David A. et al., Delayed Reaction to the Dacron Buttress Used in Urethropexy, The Journal of Reproductive Medicine, pp. 689-692, vol. 29, No. 9.

(56) References Cited

OTHER PUBLICATIONS

Richter, K., Massive Eversion of the Vagina: Pathogenesis, Diagnosis and Therapy of the "True" Prolapse of the Vaginal Stump, Clin obstet gynecol, vol. 25, pp. 897-912 (1982).
Ridley, John H., Appraisal of the Goebell-Frangenheim-Stoeckel Sling Procedure, American Journal Obst & Gynec., vol. 95, No. 5, pp. 741-721 (Jul. 1, 1986).
Roberts, Henry, M.D., Cystourethrography in Women, Deptment of Obstetrics and Gynaecology, University of Liverpool, May 1952, vol. XXXV, No. 293, pp. 253-259.
Sabre™ Bioabsorbable Sling, Generation Now, Mentor, 4 pages (May 2002).
Sabre™ Surgical Procedure, Mentor, 6 pages (Aug. 2002).
Sanz, Luis E. et al., Modification of Abdominal Sacrocolpopexy Using a Suture Anchor System, The Journal of Reproductive Medicine, vol. 48, n. 7, pp. 496-500 (Jul. 2003).
Seim, Arnfinn et al., A Study of Female Urinary Incontinence in General Practice—Demography, Medical History, and Clinical Findings, Scand J Urol Nephrol, vol. 30, pp. 465-472 (1996).
Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-125 (Apr. 2003).
Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).
Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).
Stamey, Thomas A., M.D., Endoscopic Suspension of the Vesical Neck for Urinary Incontinence in Females, Ann. Surgery, vol. 192 No. 4, pp. 465-471 (Oct. 1980).
Stanton, Stuart L., Suprapubic Approaches for Stress Incontinence in Women, Journal of American Geriatrics Society, vol. 38, No. 3, pp. 348-351 (Mar. 1990).
Stanton, Stuart, Springer-Veglag, Surgery of Female Incontinence, pp. 105-113 (1986).
Staskin, David R. et al., The Gore-Tex Sling Procedure for Female Sphincteric Incontinence: Indications, Technique, and Results, World Journal of Urology, vol. 15, pp. 295-299 (1997).
Studdiford, William E., Transplantation of Abdominal Fascia for the Relief of Urinary Stress Incontinence, American Journal of Obstetrics and Gynecology, pp. 764-775 (1944).
Subak, Leslee L. et al., Cost of Pelvic Organ Prolapse Surgery in the United States, Obstetrics & Gynecology, vol. 98, n. 4, pp. 646-651 (Oct. 2001).
Sullivan, Eugene S. et al., Total Pelvic Mesh Repair a Ten-Year Experience, Dis. Colon Rectum, vol. 44, No. 6, pp. 857-863 (Jun. 2001).
Swift, S.E., et al., Case-Control Study of Etiologic Factors in the Development of Sever Pelvic Organ Prolapse, Int Urogynecol J, vol. 12, pp. 187-192 (2001).
TVT Tension-free Vaginal Tape, Gynecare, Ethicon, Inc., 23 pages (1999).
Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, U., Female Urinary Incontinence—A Symptom, Not a Urodynamic Disease. Some Theoretical and Practical Aspects on the Diagnosis a Treatment of Female Urinary Incontinence, International Urogynecology Journal, vol. 6, pp. 2-3 (1995).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
Ulmsten, Ulf et al., Different Biochemical Composition of Connective Tissue in Continent, Acta Obstet Gynecol Scand, pp. 455-457 (1987).
Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).
Ulmsten, Ulf et al., The Unstable Female Urethra, Am. J. Obstet. Gynecol., vol. 144 No. 1, pp. 93-97 (Sep. 1, 1982).
Vesica® Percutaneous Bladder Neck Stabilization Kit, A New Approach to Bladder Neck Suspenison, Microvasive® Boston Scientific Corporation, 4 pages (1995).
Vesica® Sling Kits, Simplifying Sling Procedures, Microvasive® Boston Scientific Corporation, 4 pages (1998).
Villet, R., Réponse De R. Villet A L'Article De D. Dargent et al., Gynécolgie Obstétrique & Fertilité, vol. 31, p. 96 (2003).
Visco, Anthony G. et al., Vaginal Mesh Erosion After Abdominal Sacral Colpopexy, Am J Obstet Gynecol, vol. 184, n. 3, pp. 297-302 (297-302).
Walters, Mark D., Percutaneous Suburethral Slings: State of the Art, Presented at the conference of the American Urogynecologic Society, Chicago, 29 pages (Oct. 2001).
Waxman, Steve et al., Advanced Urologic Surgery for Urinary Incontinence, The Female Patient, pp. 93-100, vol. 21 (Mar. 1996).
Weber, Anne M. et al., Anterior Vaginal Prolapse: Review of Anatomy and Techniques of Surgical Repair, Obstetrics and Gynecology, vol. 89, n. 2, pp. 311-318 (Feb. 1997).
Webster, George et al., Voiding Dysfunction Following Cystourethropexy: Its Evaluation and Management, The Journal of Urology, vol. 144, pp. 670-673 (Sep. 1990).
Winter, Chester C., Peripubic Urethropexy for Urinary Stress Incontinence in Women, Urology, vol. XX, No. 4, pp. 408-411 (Oct. 1982).
Winters et al., Abdominal Sacral Colpopexy and Abdominal Enterocele Repair in the Management of Vaginal Vault Prolapse, Urology, vol. 56, supp. 6A, pp. 55-63 (2000).
Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).
Zacharin, Robert et al., Pulsion Enterocele: Long-Term Results of an Abdominoperineal Technique, Obstetrics & Gynecology, vol. 55 No. 2, pp. 141-148 (Feb. 1980).
Zacharin, Robert, The Suspensory Mechanism of the Female Urethra, Journal of Anatomy, vol. 97, Part 3, pp. 423-427 (1963).
Zimmern, Phillippe E. et al., Four-Corner Bladder Neck Suspension, Vaginal Surgery for the Urologist, vol. 2, No. 1, pp. 29-36 (Apr. 1994).
Mouly, Patrick et al., Vaginal Reconstruction of a Complete Vaginal Prolapse: The Trans Obturator Repair, Journal of Urology, vol. 169, p. 183 (Apr. 2003).
Pourdeyhimi, B, Porosity of Surgical Mesh Fabrics: New Technology, J. Biomed. Mater. Res.: Applied Biomaterials, vol. 23, No. A1, pp. 145-152 (1989).
Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).
Petros, Papa PE et al., An Integral Theory and Its Method for the Diagnosis and Management of Female Urinary Incontinence, Scandinavian Journal of Urology and Nephrology, Supplement 153: p. 1 (1993).
Mentor Porges, Uratape, ICS/IUGA Symp, Jul. 2002.

\* cited by examiner

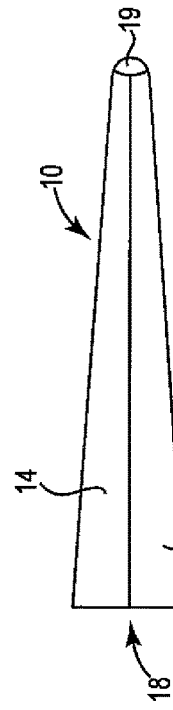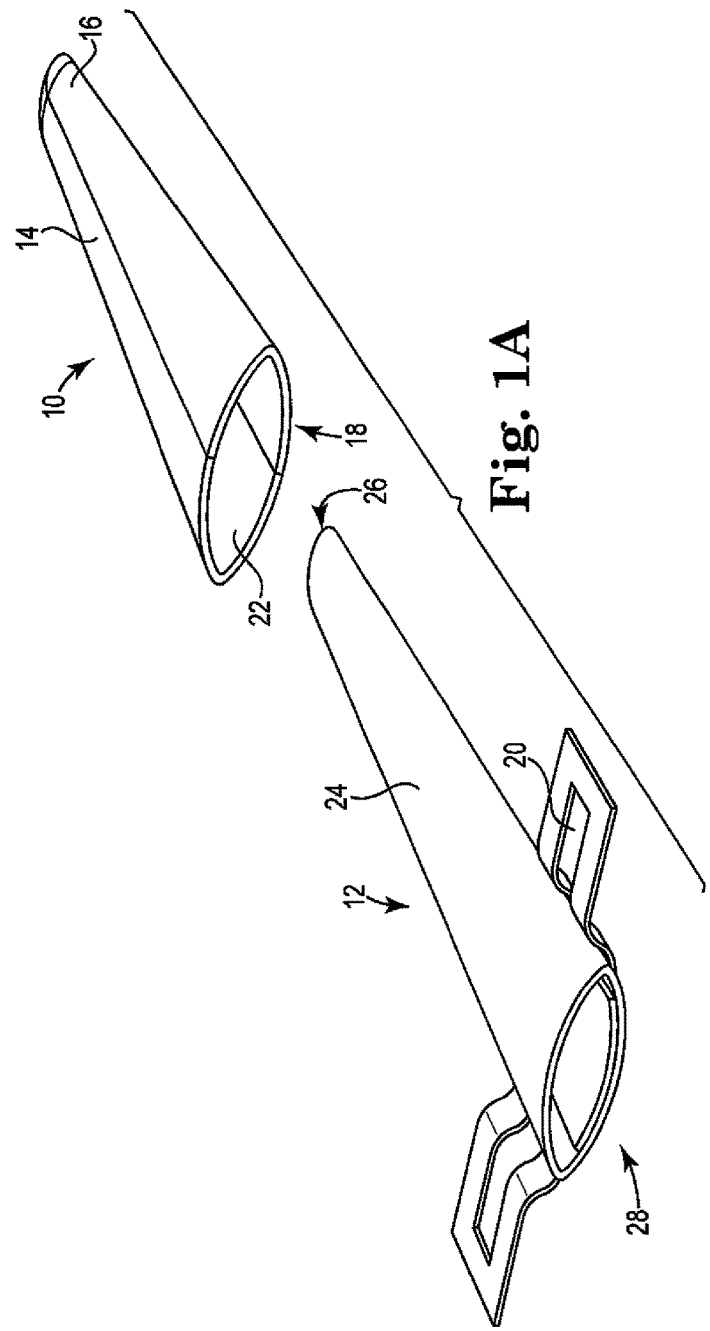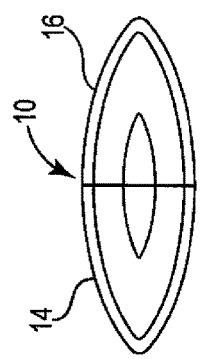

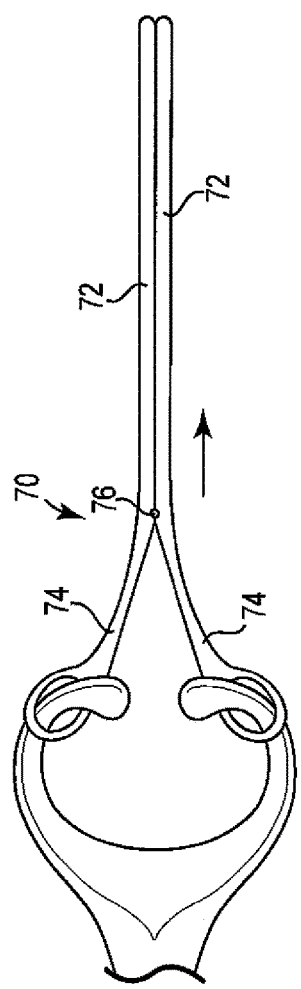
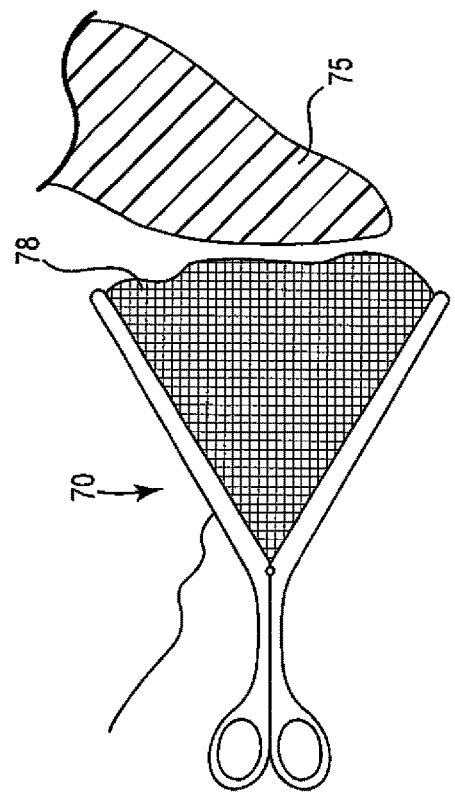
Fig. 4A
Fig. 4B

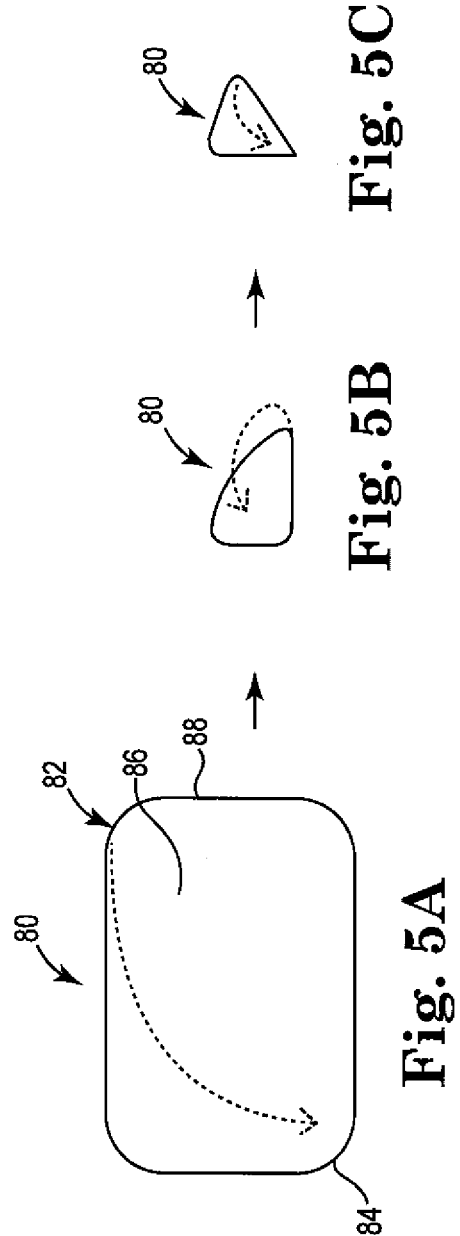

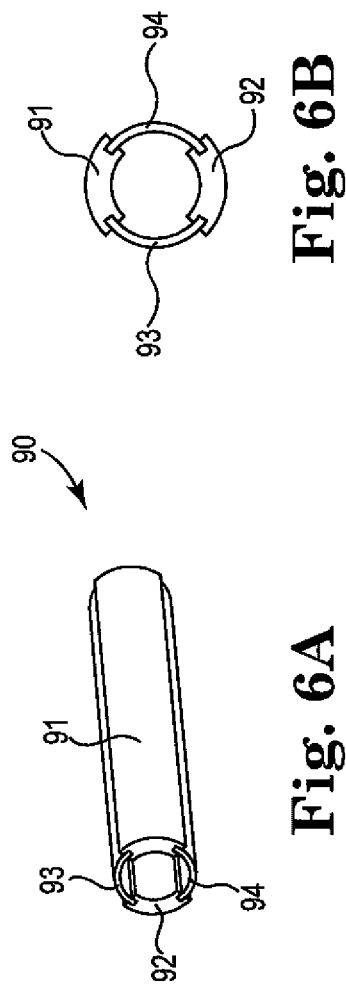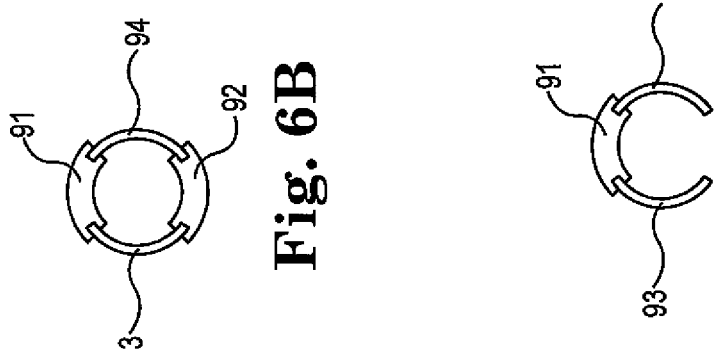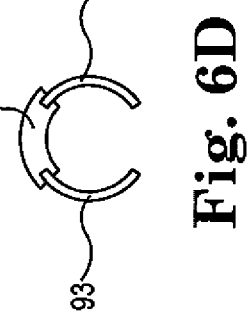

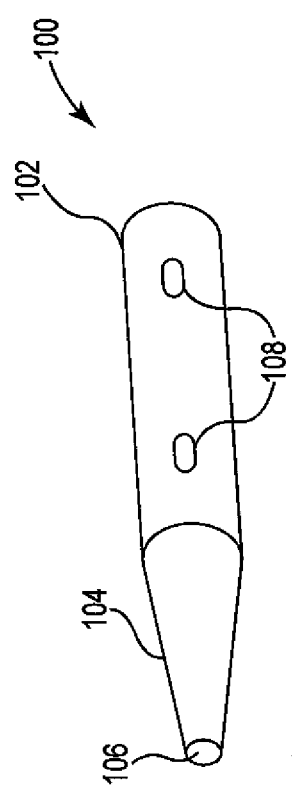

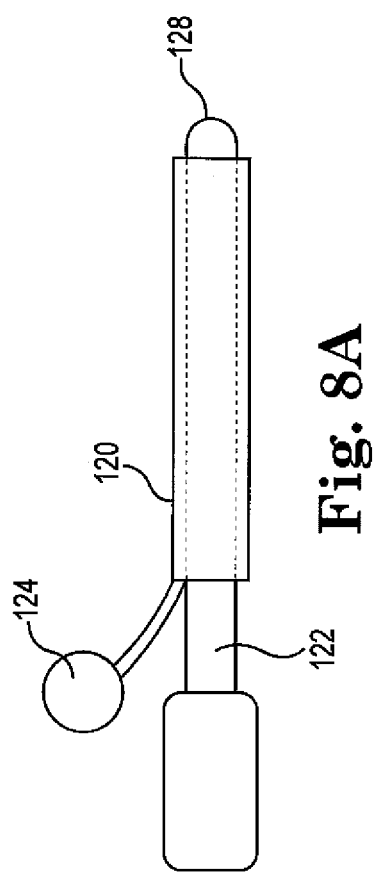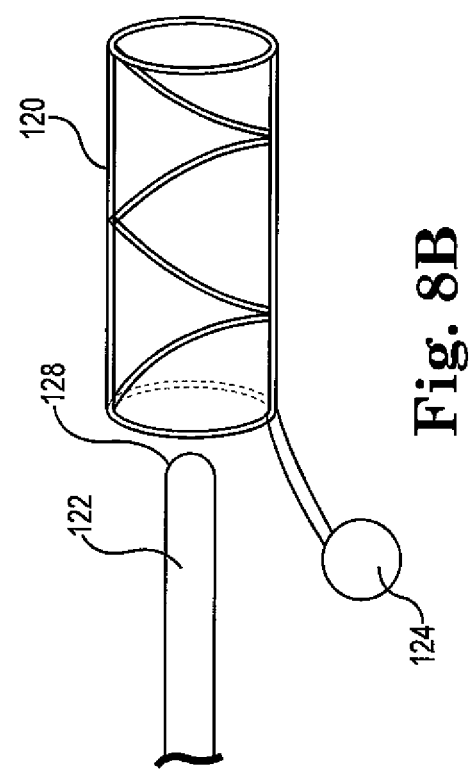

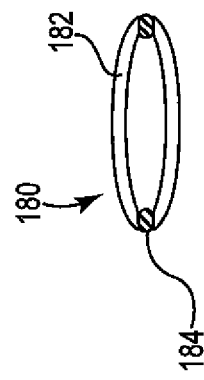
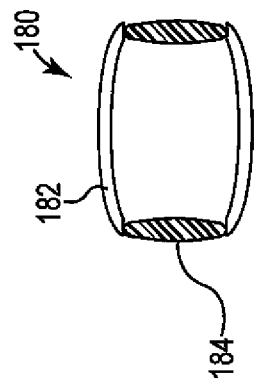
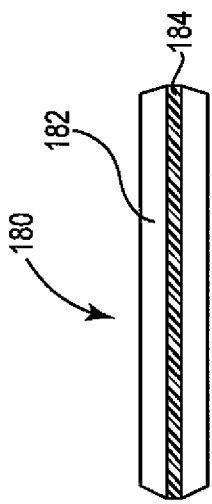
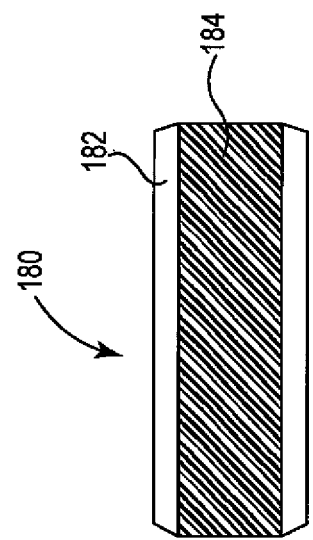

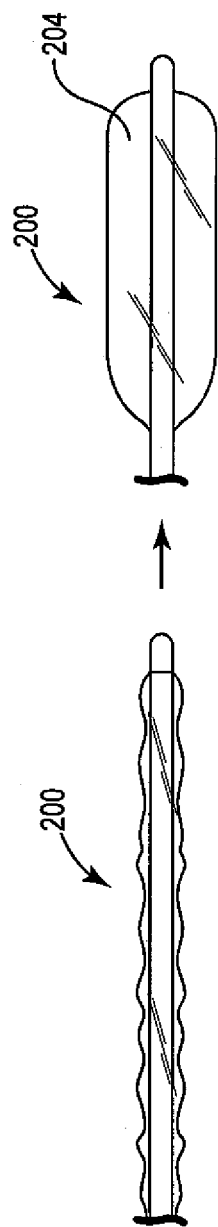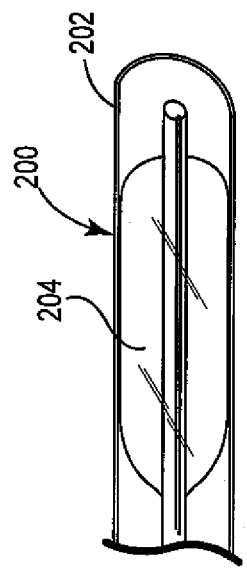

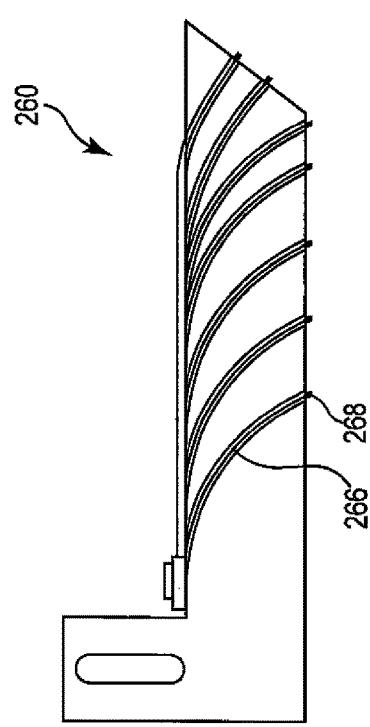
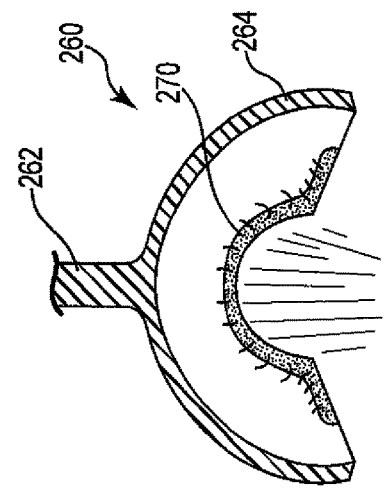
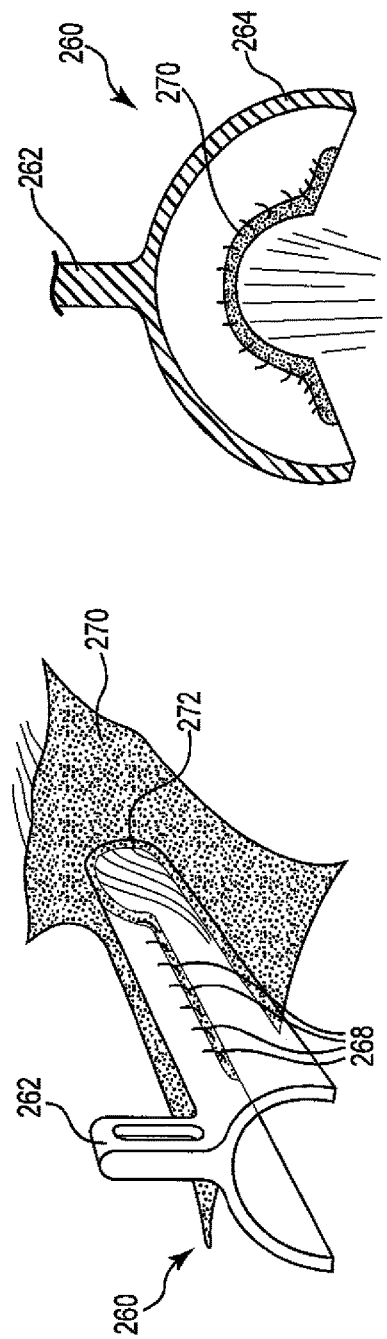
Fig. 19A
Fig. 19C
Fig. 19B

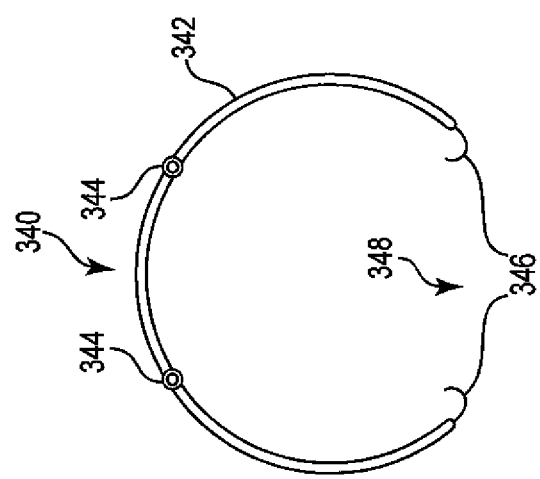

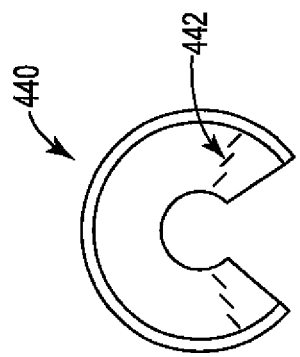
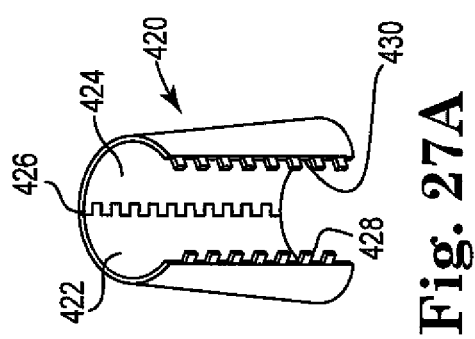
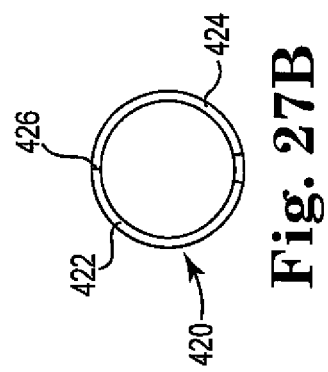

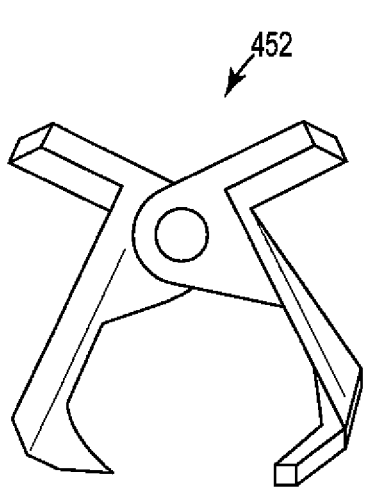
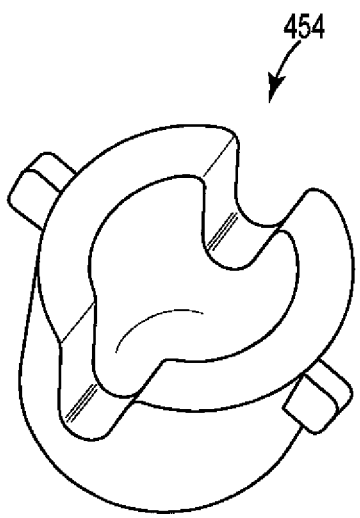
Fig. 29A    Fig. 29B
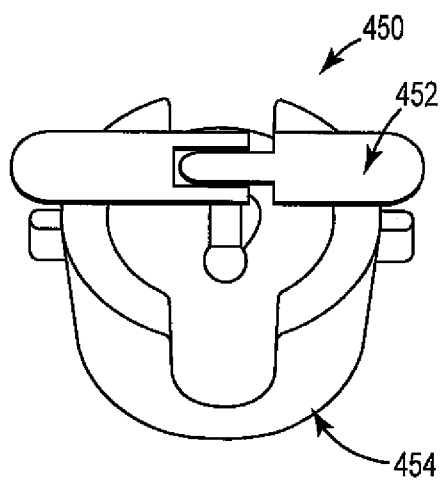
Fig. 29C

SYSTEMS, IMPLANTS, TOOLS, AND METHODS FOR TREATMENTS OF PELVIC CONDITIONS

CROSS REFERENCE TO RELATED APPLICATION

This application is a continuation of U.S. patent application Ser. No. 13/566,756, filed Aug. 3, 2012 and claims the benefit under 35 U.S.C. § 119(e) of U.S. Provisional Patent Application No. 61/515,685, filed Aug. 5, 2011 both of which are incorporated herein by reference in their entireties.

FIELD OF THE INVENTION

The present invention relates to tools and related methods for treating pelvic conditions by use of a pelvic implant to support pelvic tissue. The pelvic treatments include, for example, treatment of vaginal prolapse by laparoscopic, abdominal, and transvaginal procedures, and treatment of urethral incontinence (e.g., stress urinary incontinence) by a single incision retropubic procedure.

BACKGROUND

Pelvic health for men and women is a medical area of increasing importance, at least in part due to an aging population. Examples of common pelvic ailments include incontinence (e.g., fecal and urinary incontinence), pelvic tissue prolapse (e.g., female vaginal prolapse), and other conditions that affect the pelvic floor. Pelvic disorders such as these can be caused by weakness or damage to normal pelvic support systems. Common etiologies include childbearing, removal of the uterus, connective tissue defects, prolonged heavy physical labor, and postmenopausal atrophy.

Urinary incontinence can further be classified as including different types, such as stress urinary incontinence (STA), urge urinary incontinence, mixed urinary incontinence, among others. Urinary incontinence can be characterized by the loss or diminution in the ability to maintain the urethral sphincter closed as the bladder fills with urine. Male or female stress urinary incontinence (SUI) generally occurs when the patient is physically stressed.

Pelvic floor disorders include cystocele, rectocele, and prolapse such as anal, uterine, and vaginal vault prolapse. Vaginal vault prolapse is a condition that occurs when the upper portion of the vagina loses its normal shape and moves downwardly into the vaginal canal. In its severest forms, vaginal vault prolapse can result in the distension of the vaginal apex outside of the vagina. Vaginal vault prolapse may occur alone, such as can be caused by weakness of the pelvic and vaginal tissues and muscles, or can be associated with a rectocele, cystocele and/or enterocele. A rectocele is caused by a weakening or stretching of tissues and muscles that hold the rectum in place, which can result in the rectum moving from its usual location to a position where it presses against the back wall of the vagina. A cystocele is a hernia of the bladder, usually into the vagina and introitus. An enterocele is a vaginal hernia in which the peritoneal sac containing a portion of the small bowel extends into the rectovaginal space. All of these conditions can represent challenging forms of pelvic disorders for surgeons to treat. Some of these treatments include, for example, abdominal sacralcolpopexy (SCP), which may be performed laparoscopically, and transvaginal sacralcolpopexy (TSCP), wherein these procedures are performed using a variety of different instruments, implants, and surgical methods. It is known to repair vaginal vault prolapse by suturing the vaginal vault (e.g., by stitches) to the supraspinous ligament or by attaching the vaginal vault through mesh or fascia to the sacrum.

There is ongoing need to provide physicians with improved methods and associated instruments for treating pelvic conditions including incontinence, vaginal prolapse (e.g., vaginal vault prolapse), and other pelvic organ prolapse conditions, wherein such methods can include those that are minimally invasive, safe, and highly effective.

SUMMARY

Devices, systems, and methods as described can be used to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, hysterectomies and the like.

Certain described embodiments of devices and methods involve the use of a refractor or "expansion member" adapted to provide port access and guidance to a surgical site. These embodiments involve placement of an elongate expansion member through a body orifice or incision and to a surgical site, to create an access space from the exterior of the patient to the surgical site. The expansion member is useful to retract tissue, create an access space, and allow surgical instruments such as sharp tools to safely access the surgical site. Certain of these described embodiments relate generally to various means, devices, and techniques for providing a clear view of a surgical site in a region of a sacrum, and nearby anatomy, through a vaginal incision. In several examples, this is provided by way of a device that can be inserted into a vaginal incision and then used to expand or dilate tissue.

In described examples, desired retraction functionality is provided by a device that can be changed in its size or shape, to contact and then move, expand, or dilate (e.g., retract) tissue. An expansion member may include two or more pieces (e.g., longitudinal panels or blades) that are optionally hinged or slidably connectable and able to move laterally or longitudinally relative to each other. The pieces can be moveable relative to each other in a manner that allows the pieces to define a space (access space) therebetween, the space being capable of being varied in size, e.g., "expandable." In specific embodiments, the device can be inserted into a vaginal incision and then expanded, dilated, manipulated, or otherwise used for tissue retraction to create a working space between the vaginal introitus and the vaginal apex, a posterior location of a pelvic region, or a region of sacral anatomy. Certain preferred versions of these tools can include distal end functionality to add efficiency to a surgical procedure, such as a lighting feature, an anchor driving feature, an optical feature that allows viewing of the surgical site, or hooks and/or other attachment features.

Certain described embodiments relate to surgical tools having one or more surfaces capable of retracting tissue (a retractor, such as an expansion member), and adapted to provide access and guidance to a surgical site. These embodiments involve various surgical tools and related methods designed to provide improved and safer access to a surgical site or anatomy, for example so that sharp objects and tools can be passed to a surgical location without having to make multiple attempts from an incision to an anatomical target area. Certain of these described embodiments relate generally to various means, devices, and techniques for providing a clear view and unobstructed access to a surgical site. In several examples, this is provided by way of an expandable device, or other devices capable of being used to retract tissue, that can be inserted into an incision site and then expanded, dilated, manipulated, or otherwise used for tissue retraction. Certain preferred versions of these tools can include distal end functionality to add efficiency to a surgical procedure.

BRIEF DESCRIPTION OF THE DRAWINGS

The present invention will be further explained with reference to the appended Figures, wherein like structure is referred to by like numerals throughout the several views, and wherein:

FIGS. 1A-1C are perspective, top, and side views, respectively, of an embodiment of a retractor and introducer system of the invention;

FIGS. 4A and 4B are top views of a retractor of the invention, illustrated in closed and open configurations, respectively;

FIGS. 5A-5C are top views of an embodiment of a retractor;

FIGS. 6A and 6B are perspective and end views, respectively, of a retractor embodiment in a first configuration, and FIGS. 6C and 6D are perspective and end views, respectively, of the same retractor embodiment in a second configuration;

FIG. 7 is a perspective view of a retractor embodiment of the invention;

FIGS. 8A and 8B are schematic front views of a retractor and introducer of the invention;

FIGS. 12A and 12B are front and side views, respectively, of a retractor in a collapsed state;

FIGS. 13A and 13B are front and side views, respectively, of the retractor of FIGS. 12A and 12B in an expanded or open state;

FIGS. 14A and 14B are front views of an embodiment of a retractor and introducer;

FIG. 19A is a perspective view of a retractable hook system for use with a retractor of the invention;

FIG. 19B is a perspective view of a retractor positioned relative to a peritoneum;

FIG. 19C is an end view of the retractor of FIG. 19B;

FIG. 23 is a top view of an embodiment of a retractor of the invention;

FIGS. 27A and 27B are top perspective and top views, respectively, of a retractor of the invention;

FIG. 28 is a side view of an embodiment of a retractor;

FIGS. 29A-29C are top perspective views of an anchor, a ring, and an anchor and ring system of the invention, respectively.

DETAILED DESCRIPTION

Figure 2:
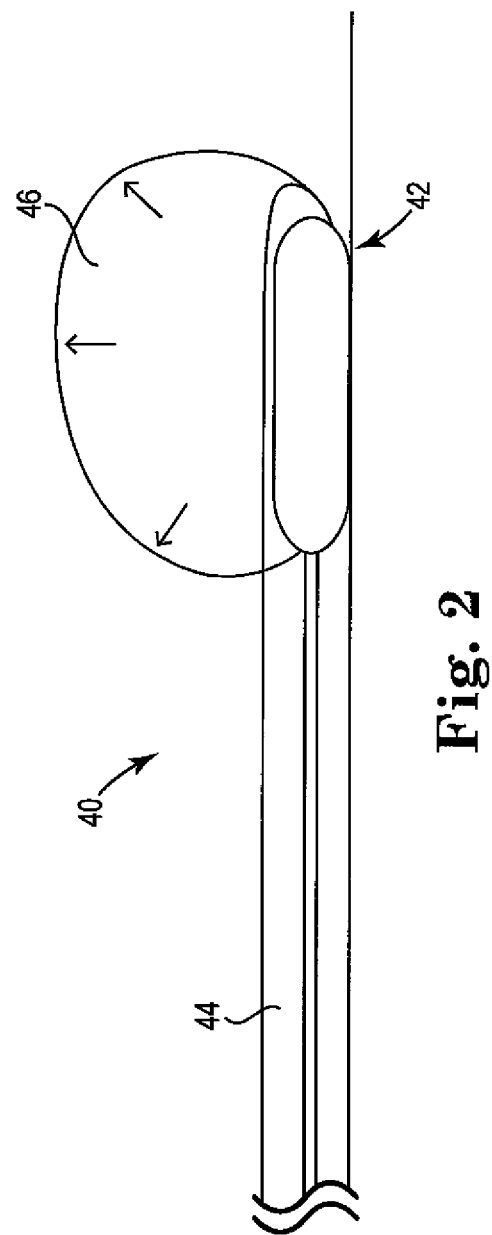
FIG. 2 is a side view of a retraction tool of the invention.

Pelvic floor disorders include cystocele, rectocele, enterocele, uterine and vaginal vault prolapse, urinary and fecal incontinence, among others, in men and women. These disorders typically result from weakness or damage to normal pelvic support systems. The most common etiologies include childbearing, removal of the uterus, connective tissue defects, prolonged heavy physical labor, and postmenopausal atrophy.

Vaginal vault prolapse is often associated with a rectocele, cystocele, or enterocele. It is known to repair vaginal vault prolapse by suturing to the supraspinous ligament or to attach the vaginal vault through mesh or fascia to the sacrum. Many patients suffering from vaginal vault prolapse also require a surgical procedure to correct stress urinary incontinence that is either symptomatic or latent.

A sacral colpopexy is a procedure for providing vaginal vault suspension. It may be performed through an abdominal incision, a vaginal incision, or laparoscopically and entails suspension (by use of an implant such as a strip of mesh) of the vaginal cuff to a region of sacral anatomy such as the sacrum (bone itself), a nearby sacrospinous ligament, uterosacral ligament, or anterior longitudinal ligament at the sacral promontory. In some sacral colpopexy procedures that also involve a hysterectomy, an implant can attach to posterior vaginal tissue remaining after removal of the uterus and cervix, and attaches also to anatomy to support the vaginal tissue, at or around the sacrum such as to uterosacral ligaments or to the sacrum itself (i.e., to a component of the sacral anatomy).

As used herein, the term "anchor" refers non-specifically to any structure that can connect an implant to tissue of a pelvic region, to secure the implant to that tissue. The tissue may be bone, or a soft tissue such as a muscle, fascia, ligament, tendon, or the like. The anchor may be any known or future-developed structure, or a structure described herein, useful to connect an implant to such tissue, including but not limited to a clamp, a suture, a soft tissue anchor such as a self-fixating tip, a helical anchor such as a screw-type or corkscrew-type anchor that can be driven into bone or soft tissue using rotation, a bone anchor (e.g., screw), or other structures known or later developed for connecting an implant to soft tissue or bone of a pelvic region.

Traditional pelvic implant installation procedures (e.g., sacral colpopexy procedures) may be performed through an abdominal opening or laparoscopically. As such, special skills and equipment are needed to complete the procedure effectively. And abdominal wounds are created. According to methods described herein, a tissue expander or other retractor devices and tools can be used according to minimally invasive sacral colpopexy procedures with no abdominal wounds or potential organ perforation or dissection. Examples of similar methods and tools, expansion members, and soft tissue anchors (which may include structures or features similar to those herein) are described in Assignee's co-pending International Patent Application having International Patent Application number PCT/US2010/062577, filed Dec. 30, 2010, the entirety of which is incorporated by reference.

As described, a retractor or expansion member may include distal end functionality such as an anchoring functionality, viewing and lighting functionalities, size adjustability, suction, dissection, anchor delivery, implant delivery, and fluid delivery, among others. By use of a retractor or expansion member having viewing and lighting functions, clear visualization of internal tissue is provided for placement and anchoring of an implant, e.g., to a region of sacral anatomy. A physician is able to guide a distal end or shaft of an implant delivery tool (i.e., "needle") to a surgical location, with direct viewing, is able to visually identify potential areas of risk and guide or steer the tool to a desired target tissue site, e.g., for placing an anchor or implant. With a visualization feature, a faster learning curve is provided for physicians to safely pass the needle with the aid of a scope and optical viewing, and the knowledge from scope usage in surgery is applied to and benefits surgical procedures.

According to presently described systems, devices, and methods, an expansion member, "retractor," or "speculum," or the like can be useful for accessing a male or female pelvic anatomy during a pelvic procedure, especially a female pelvic anatomy, to access tissue of the posterior pelvic region such as to perform a sacral colpopexy procedure. An expansion member or other tool can optionally have a length to allow such access when placed transvaginally, e.g., a length to allow a distal end of the tool to access pelvic tissue while a proximal end of the tool extends through a vaginal opening and to a location external to the patient. The proximal end of the tool remains external to the patient during use to allow a surgeon or other user to access and manipulate the proximal end and access a surgical site at the distal end. A shaft extends between the distal and the proximal ends, and may optionally include an enclosure or tube along some or all of the length.

According to certain embodiments, a retractor or expansion member can optionally include a shaft portion that includes a full or partial enclosure or "tube" (whether a partial tube or complete tube) to provide partial or continuous structure and support along a length of the tool between the distal end and proximal end, to separate tissue from a working space. The structure may extend lengthwise along a partial or complete length of the device, and in a lateral direction the structure can be a complete or partial structure; the structure may be in the form of a tube, having structure extending around a complete circumference, e.g., a circular or non-circular "tube"; or a structure that extends partially around a circumference, such as in the form of a partial circular or non-circular "tube." A diameter of such a structure can be useful to allow the device to be inserted and placed with reduced trauma. Optionally, as described elsewhere herein, a diameter of the tube can be variable, such as by being expandable after placement of the tube within a patient, to allow increased and expanded access to tissue at a surgical site.

Exemplary tools that can be used in combination with various retractors or expansion members can include one or more functional features at a distal end that allow the tool to be useful to carry out functions such as dissection (a mechanical dissection using a sharp blade, a blunt dissection device using an expandable structure such as a balloon, hydrodissection, etc.), blunt dissection, viewing (visualization) of a surgical location, illumination of a surgical location, fluid delivery at a surgical location, irrigation at a surgical location, suction at a surgical location, expandability, and placing anchors (bone anchors, soft tissue anchors such as a self-fixating tip, sutures, etc.) into a desired target tissue at a surgical location.

Various embodiments of tools (e.g., retractors, expansion members, etc.) are described hereinbelow, and may have general structural and operational features that allow one or more flexible, rigid, or semi-rigid, distal retracting structure to be introduced through an incision (e.g., a vaginal incision), to retract internal tissue. In certain (but not all) embodiments the tool can be introduced through an incision in a closed, compressed, or reduced-size or reduced-diameter state, then be moved, assembled, or expanded to enlarge a cross-sectional size or related space or opening to push tissue aside to create space in and access to a pelvic region with access to desired anatomy. In other embodiments, the tool may have a variable diameter along the length, tapered from a smaller diameter at a distal end to a larger diameter at a proximal end.

For tools of variable diameter, a preferred size of a device can include a cross sectional dimension (e.g., a width or diameter associated with an opening along a length of the device) in the range from 1 to 5 centimeters, such as from 2 to 4 centimeters, when retracting structures are in their a reduced-size configuration. Upon opening, un-compressing, expanding, or assembling, etc., the retracting structures, a preferred dimension (e.g., a width or diameter associated with an opening along a length of the device) associated with these structures can be in the range from 2 to 10 centimeters, such as from 3 to 7 centimeters.

Various embodiments of devices ("expansion members," "retractors," or "speculums") are contemplated for use in providing access to internal tissue of a pelvic region through an incision in a male or female patient, e.g., as a tissue retractor used to gain access to a posterior region of a pelvic anatomy. Any of these may be useful according to methods for placing an implant to support pelvic tissue, for example a SCP procedure, using any desired or useful implant, insertions tool, multi-functional tool, anchor, etc.

According to certain embodiments, an expansion member can be designed to have a reduced cross-sectional size and profile in closed or compressed state for easy entry into a patient (e.g., vaginally), and the expansion member can be opened or expanded to open and retract the surrounding tissue for improved viewing of the surgical area to keep tissue from interfering with the procedure. In particular such embodiments, a device can include multiple (e.g., three) retractor surfaces, each surface being separated longitudinally by a hinge. The hinge extends partially or fully along the length of the expansion member, between a distal and a proximal end, and a hinge may be straight or curved.

Referring now to the Figures, where like structure may be described with like reference numbers and/or terms, and initially to FIG. 1, an embodiment is illustrated of a retractor assembly that includes an introducer 10 and a retractor 12.

The introducer 10 is a component that can be inserted into a patient (e.g., through a vaginal introitus) to provide an initial opening of a surgical space. The retractor 12 can then be placed within the installed introducer 10, and the introducer can be removed. In the illustrated embodiment, the introducer 10 includes a first section 14 and a second section 16, which may roughly be configured such that each of the sections 14, 16 comprises one half of the total width of the introducer 10, although the division of size between the two sections may be different. All or portions of the introducer 10 can be made of a transparent or translucent material in order to be able to view the insertion of a retractor or other components into its internal area, for example. The introducer 10 may further include a proximal end 18 and a polished tip 19 at the opposite end from the proximal end 18 to allow for viewing at the distal end during insertion of the introducer 10. Once the introducer 10 is placed within a patient in a desired location, the retractor 12 can be placed inside of the introducer 10 at its proximal end 22 and then the introducer 10 can be removed. The retractor 12 can include handles 20, which can optionally be foldable relative to the retractor body and positioned at or adjacent to its proximal end 28. In certain embodiments, the introducer 10 can be disassembled and removed from the patient as separate pieces (e.g., first and second sections 14, 16). The retractor 12 can then be opened or expanded to create a larger surgical space. The expandable retractor 12 can be expanded (opened) and contracted (closed) by any desired mechanism, as described herein or otherwise.

FIG. 2 shows an example of a method and a device 40 useful to retract tissue internal to a patient, including a speculum 44 having a "blunt dissection device" 46 at its distal end 42. The device 40 can be used in combination with a viewing apparatus capable of viewing the distal end during placement. The viewing apparatus may be any apparatus capable of optically accessing the distal end while the distal end is being placed within a patient (e.g., a fiber optic device or a mirror at the end of an extension arm). The distal end includes the blunt dissection feature 46 or surface that can be used to contact tissue, to cause dissection or otherwise move or retract tissue by manipulation of the handle at the proximal end. The blunt dissection surface may include one or a combination of a rigid, curved or flat paddle, and an optional expandable structure or surface. A preferred expandable structure may be an inflatable balloon (e.g., air, carbon dioxide, nitrogen, etc.), which in use can be placed in contact with tissue and expanded to adjust the position of tissue, e.g., retract the tissue during a surgical procedure. The distal end can also optionally and preferably include a light, for better viewing of a surgical space by a surgeon.

Figure 3:
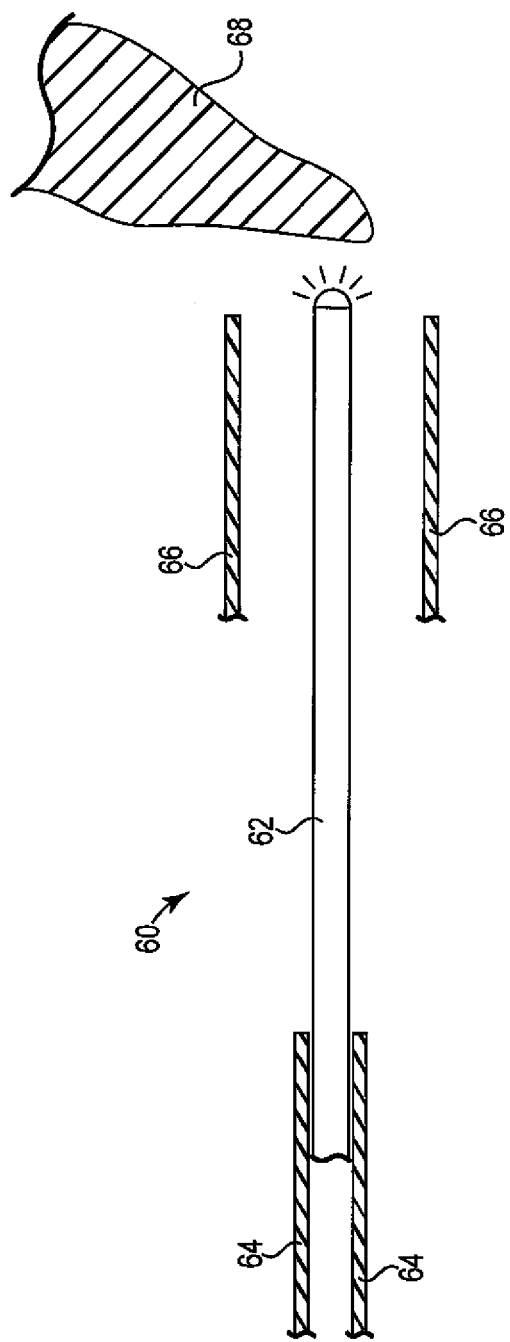
FIG. 3 is a side schematic view of a retractor of the invention as it can be positioned relative to a patient's anatomy.

FIG. 3 shows another embodiment of a retractor 60 having an expandable surface, and which optionally includes a fiber optic feature such as a fiber optic wand 62 that can be used to view the distal end of the retractor during use in a surgical procedure. The distal end of the wand 62 is shown as being positioned next to the sacrum 68 of a patient, although the wand 62 can instead be used in another location in the patient. The fiber optic wand 62 can also be used as an introducer that is inserted into a surgical site as a guide for subsequent placement of a retractor. The retractor may be of the type that can be inserted in a collapsed or closed state, as shown with the configuration of retractor 60 in a non-expanded retractor configuration 64. The retractor 60 can then be expanded within the patient to create a surgical space, as shown with the configuration of retractor 60 in an expanded retractor configuration 66.

FIGS. 4A and 4B illustrate another exemplary embodiment of an expandable retractor 70, which includes a structure that is configured similar to the general configuration of a pair of scissors. In particular, retractor 70 includes handles and arms 74 extending proximally from a pivot point 76, and also includes elongate arms 72 extending distally from pivot point 76. Due to the configuration of the handles and arms, movement of the arms 74 toward each other will cause the elongate arms 72 to move away from each other, and movement of the handles 74 away from each other will cause the elongate arms 72 to move toward each other. The retractor 70 is further provided with a sheet of material 78 operatively attached to the elongate arms 72 so that the material 78 will be compressed or compacted when the arms 72 are relatively close to each other, and so that the material 78 will be extended or spread to cover at least a portion of the space between the arms 72 when the arms are moved away from each other. The sheet of material 78 can be a mesh material, a net (e.g., light fabric), or other film (e.g., polymeric) material. In operation, the retractor 70 can be inserted into a patient, such as in a location adjacent to a sacrum 75, for example, and then expanded to retract the surrounding tissue. When the retractor is in its expanded configuration, the material 78 will be spread between the arms 72 to control or retract tissue.

FIGS. 5A-5C illustrate a collapsible tissue retractor 80, which generally includes an outer frame 88 surrounding a thin flexible material piece 86. The frame 88 may be made of a separate material, such as a thin wire or other flexible material, or the frame may instead be provided as a reinforced area that surrounds the material piece 86. That is, the structure of the retractor 80 can include a perimeter (edges) along a length that includes structural reinforcements such as a folding scaffold or collapsible wire. In any case, the retractor 80 is one that in a collapsed form is folded, twisted, or spirally wound, and that can be expanded by unfolding or by expanding the spiral. For one example, one corner area 82 of the retractor 80 can be folded or twisted toward an opposite corner area 84, as is shown by the arrow in FIG. 5A. FIGS. 5B and 5C illustrate other exemplary manipulations of the retractor 80 that can be performed to reduce its outer dimensions. In one exemplary use of the retractor 80, retractor 80 is compressed to a desired size so that it can be inserted into a particular area that is to be expanded. After it is in place, retractor 80 can be untwisted or uncoiled so that it expands to cover a larger area and also causes corresponding movement of the surrounding tissue (e.g., bowel tissue)

FIGS. 6A-6D illustrate an expansion member or retractor 90 that comprises multiple sections that extend from each other to form a ring-like structure. In this illustrated embodiment, the retractor 90 includes four of such sections, shown as sections 91-94 in FIGS. 6A and 6B, wherein sections 91 and 92 are on opposite sides of retractor 90, and wherein sections 93 and 94 extend between the sections 91 and 92 and are also opposite sides of the retractor from each other. Adjacent sections of the retractor 90 can be attached to each other in any number of different ways, such as with a mechanical connection (e.g., dovetailed ends, frictional fit, and the like), an adhesive connection (e.g., with a breakable adhesive bond between edges of adjacent sections), or another connection method or combination of connection methods. The sections of the retractor 90 can be assembled or attached to each other somewhere that is external to the patient, and then the retractor 90 can be inserted into a target location where it is desired to retract tissue. In this way, the retractor will have a relatively smooth outer surface that does not have exposed free edges that can interfere with tissue that is encountered during insertion of the retractor into the patient.

As illustrated in FIGS. 6C and 6D, one of the sections (e.g., section 92) can be removed to create a length-wise opening or slot along a side of the retractor 90 that allows access to tissue of the patient along a length of the expansion member, when installed. Removal of this section can be accomplished by breaking any seals on both edges of sections that are adjacent to the section to be removed, and then sliding that section out of the patient. The illustrated embodiment includes a substantially circular cross-section, but other non-circular shapes may also be useful.

FIG. 7 shows an expansion member or retractor 100 that includes a shaft 102 with a hollow interior having a distal end and a proximal end, and a blunt tip member 104, which includes a blunt distal tip 106, that can be removably mounted to the distal end. The expansion member 100 can be placed into a patient with the blunt tip member 104 attached to the distal end, then the blunt tip member 104 can be removed and withdrawn through the shaft. Optionally and as illustrated, the shaft 102 may include lights 108 that are provided to illuminate a surgical space at the distal end, wherein such lights 108 can be mounted on the inside of the shaft 102. At least a portion of the blunt tip member 104 may optionally be transparent, and can have an open or closed tip. The illustrated embodiment includes a substantially circular cross-section, but other non-circular shapes may also be useful.

FIGS. 8A and 8B illustrate a combination of an introducer 122 and an inflatable retractor 120. Introducer 122 includes a distal tip 128, which can be guided and held in position relative to a target tissue of a patient. The introducer and retractor combination can be inserted into a patient (e.g., through a vaginal introitus) to provide an initial opening of a surgical space. A pump 124 of the retractor 120 can then be activated to inflate and expand the outer tubular shape of the retractor 120 to create a surgical space in the patient. After inflation of the retractor 120, the introducer 122 can be removed from the target tissue of the patient.

Figure 9:
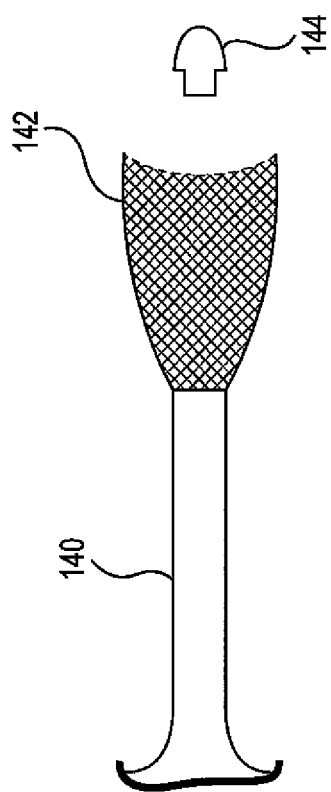
FIG. 9 is a front view of a retractor and introducer embodiment of the invention.

FIG. 9 illustrates an introducer 140 with a self-expanding (e.g., nitinol) or shape-memory stent or structure 142 extending from its distal end. To maintain the structure 142 in a compressed configuration, it can be kept in a deployment tube or other structure of the introducer that can be moved relative to the structure 142 when it is desired to allow it to expand. This embodiment further includes a dissolvable or disposable tip 144 (e.g., rounded) that can also help to maintain the stent 142 in a closed (collapsed) state during introduction into a patient. The stent 142 is biased toward an open (i.e., non-collapsed, or "deployed") state, which has a reduced length and increased diameter, and can be collapsed and extended to a non-deployed state having a greater length and reduced diameter. The non-collapsed (deployed) stent 142 can be collapsed (closed) and lengthened by placing lateral pressure on the stent surface, such as at an end or a location along the length of the stent. For example, the stent 142 can be placed and maintained in the collapsed state using the introducer, and by the use of a removable or dissolvable tip 144 at one end (e.g., the distal end). In use, an introducer can be used to place the stent 142 in a patient in the collapsed state. The introducer can be withdrawn, and the tip 144 can be removed or dissolved, allowing the stent 142 to expand within the patient. The stent 142 can be designed to provide a working depth and a working space as described herein.

Figure 10:
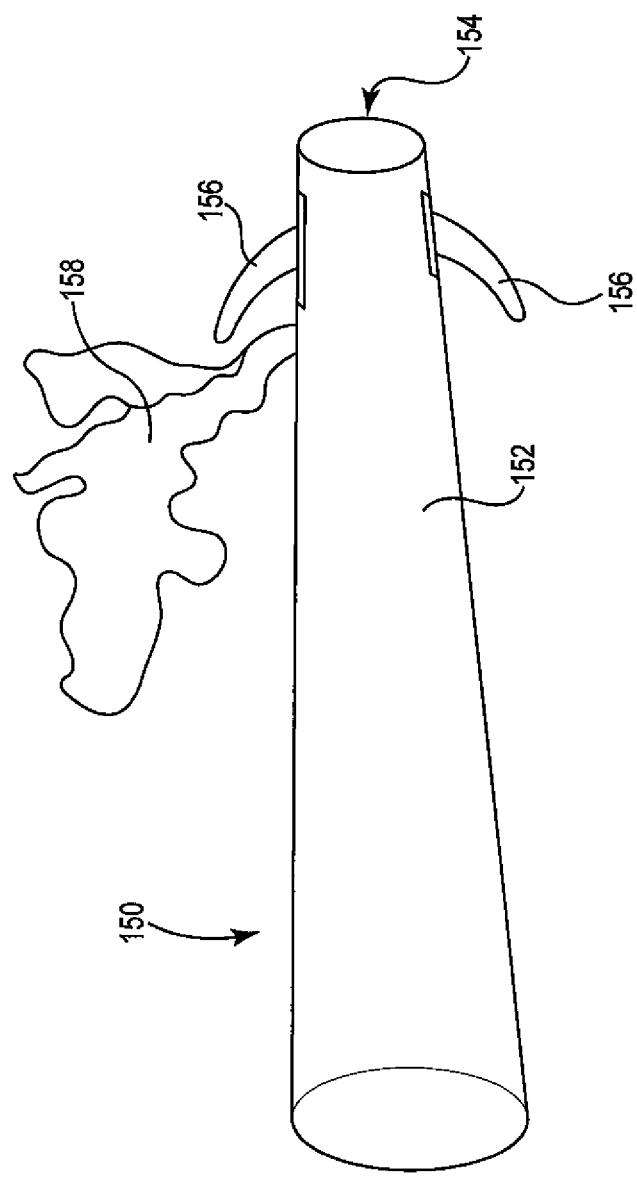
FIG. 10 is a perspective view of a retractor of the invention.

FIG. 10 illustrates an example of a retractor 150 that includes a retractor body 152 that may be shaped as an elongated cylinder, for example, and one or more distal end extensions 156 adjacent to a distal end 154 of the body 152. The extensions 156 can be fixed or moveable relative to the body 152, and can be used to push tissue aside without damaging it when inserting the distal end of the retractor 150 into a patient at a surgical site. The extensions 156 can be shaped like a fin, a paddle, or another extension structure that can be manipulated by rotating the body 152 within the patient to gently push tissue aside. The extensions 156 can have a wide variety of shapes, such as straight, curved, or bent, and may extend directly away from the body 152 or may be angled toward or away from the distal end or the proximal end. The structure of the extensions 156 can be sufficiently rigid to move tissue, but can optionally be soft or malleable enough to avoid damaging the tissue, such as can be accomplished by using extensions that have a shape that is relatively blunt and without sharp edges. Optionally, the extensions 156 can be moveable relative to the body 152 by manipulation of an actuator at or near the proximal end of the retractor 150.

Figure 11:
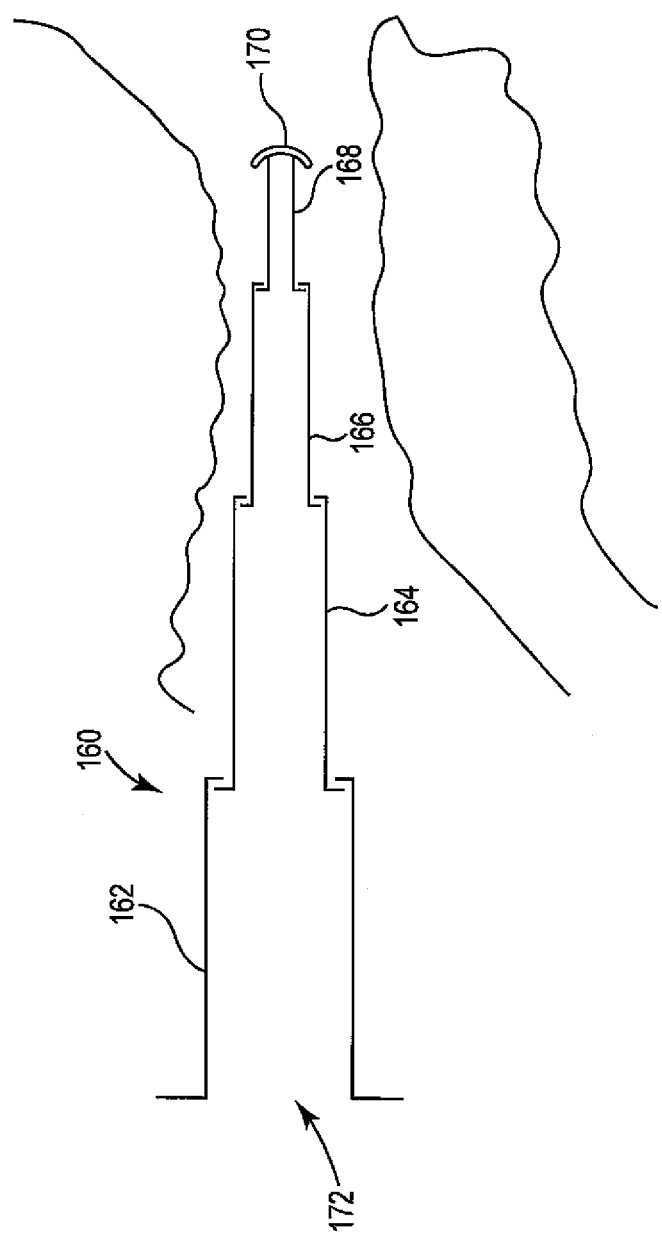
FIG. 11 is a front view of a retractor of the invention in an exemplary location relative to a patient's anatomy.

FIG. 11 illustrates another exemplary embodiment of an expansion member or retractor 160. Retractor 160 includes multiple sections or segments of different cross-sectional size (e.g., diameter) along its length, each of which has a proximal end and a distal end arranged so that the sections can be assembled by connecting a distal end of one section to a proximal end of an adjacent section. In this particular illustrated embodiment, the retractor 160 includes four segments 162, 164, 166, 168, each of which has a progressively smaller cross-sectional diameter than the previous segment. It is understood that a retractor of this type can have more or less than four of such segments. The multiple segments can be assembled in a "telescoping" manner, with the most distal segment 168 having the smallest diameter and the most proximal segment 162 having the largest diameter. The distal segment 168 can optionally include a lens 170 at its distal tip, wherein this lens 170 can be a clear, polymeric material, for example, and can include a fisheye or wide-angled configuration.

The assembled expansion member 160 can be inserted into a patient until it is positioned with its distal end segment 168 is located at a desired surgical site (e.g., near a sacrum). Optionally, the smaller-diameter segments can be removed, and one of the larger-diameter, or the largest-diameter segment 162 can be placed to extend to the surgical site. For example, the smaller sections can be removed through the largest section and the largest diameter section can be advanced to extend to the surgical site, so the site is expanded to the larger diameter of the largest-diameter section.

FIGS. 12A and 12B illustrate an exemplary embodiment of an expansion member 180, wherein FIGS. 12A and 12B show the expansion member 180 in its collapsed state, and wherein FIGS. 13A and 13B show the expansion member 180 in its expanded or open state. Expansion member 180 includes longitudinal segments or sides 184 of an expandable member (e.g., balloon), and other longitudinal members or sides 182 of a rigid material. The two opposing rigid sides 182 are connected to each other at their end areas by the two opposing expandable sides 184 (e.g., comprising inflatable balloons). In use, the expansion member 180 in a closed or collapsed state can be inserted into a patient to place a distal end at a surgical site. During or upon insertion, the expandable sides 184 can be expanded (e.g., inflated) to move the expansion member to an open or expanded state, which will include moving the rigid sides 182 outwardly in response to the expansion of the expandable sides 184.

FIGS. 14A and 14B illustrate a system that includes an introducer 200 and a retractor 202, wherein the introducer 200 is expandable. For example, the expandable introducer 200 can include a balloon 204 or other expandable structure that is capable of being expanded (e.g., inflated) within a patient to displace or retract tissue. In use, the introducer 200 can be inserted into a patient in a non-expanded state, as shown on the left side of FIG. 14A. The introducer 200 can then be expanded, as shown on the right side of FIG. 14A. Thereafter, the retractor 202, which may comprise a rigid tube, for example, can be placed over the expanded introducer 200. The introducer 200 can then be collapsed (e.g., deflated) and removed from the patient, leaving the rigid retractor 202 in place to provide access to a surgical site.

Figure 15A:
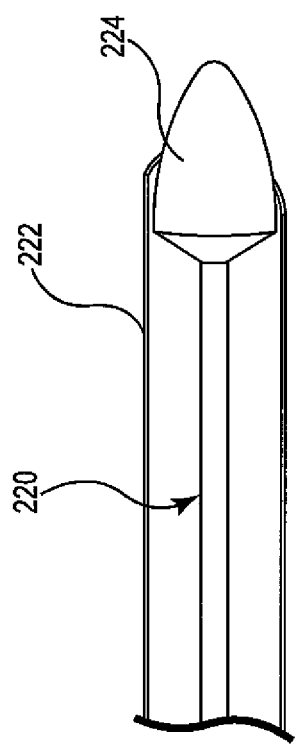
FIGS. 15A and 15B are front views of a retractor of the invention.
Figure 15B:
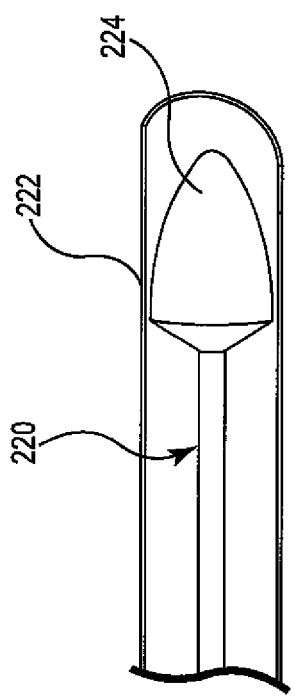

FIGS. 15A and 15B illustrate another embodiment of a system that includes an introducer 220 and a retractor 222, the introducer 220 including a dilating tip 224, which may have a curved or blunt distal end and a circular or curved cross-section (when viewed in a longitudinal direction), such as in the shape of a curved "bullet" or blunt-tipped "cone". Such a configuration of the dilating tip 224 is provided so that when it is advanced into tissue, it will deflect and displace the tissue laterally to expand an opening for introducing the retractor 222. The dilating introducer 220 can be advanced into tissue, through an incision to displace or retract tissue extending to a surgical site. The rigid expansion member (e.g., tube) 222 can closely following the dilating tip 224, or can subsequently be placed into the opening made by the dilating tip 224. The introducer 220 can then be removed, leaving the rigid retractor 222 in place to provide access to a surgical site.

Figure 16A:
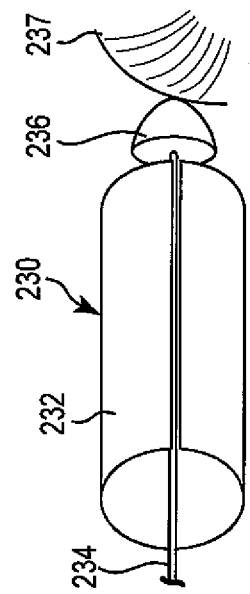
FIGS. 16A and 16B are perspective views of a retractor of the invention.
Figure 16B:
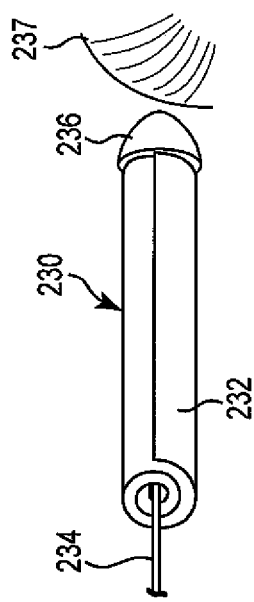

FIGS. 16A and 16B illustrate an example of an expansion member 230 that includes an expanding portion 232 and a blunt dilating tip 236. Generally, the structure includes an introducer having an inner shaft 234 and an expandable structure 232 (e.g., expandable retractor) removably attached to the inner shaft 234. The introducer carries the expandable structure 232 to a desired location (e.g., a sacrum 237), at which location the expandable structure 232 can be expanded and the inner shaft can be withdrawn. The expandable structure 232 can have a number of different expandable configurations, such as a coiled surface that can expand laterally as it uncoils, or an inflatable surface (e.g., balloon), such that the expanding structure can be inserted into a patient and expanded laterally to displace tissue to create a surgical incision. The distal end may include an optional blunt or dilating tip 236 that can deflect and displace tissue as the tip is advanced through a surgical incision and toward a surgical site. As illustrated, the expandable structure 232 can be expanded to produce an expansion member or retractor that can be left behind in the patient to allow access to the surgical site.

In use, the expansion member 230 can be inserted into an incision with the expandable structure 232 in a collapsed or closed state, and the dilating distal end can be advanced through tissue and positioned at a surgical site (e.g., a region of a sacrum 237). The distal end may optionally include fiber optics, an electronic camera, or other mechanism to allow visualization at the distal end for guiding the expansion member during insertion. Once placed as desired, the expandable structure 232 can be expanded to displace tissue along the length of the shaft, which can generally correspond to a path leading to a surgical site. The expandable structure 232 can be separated from the blunt tip and inner shaft, and the inner shaft and blunt tip can be removed, leaving the expanded structure to function as a retractor to provide access to the surgical site.

Figure 17:
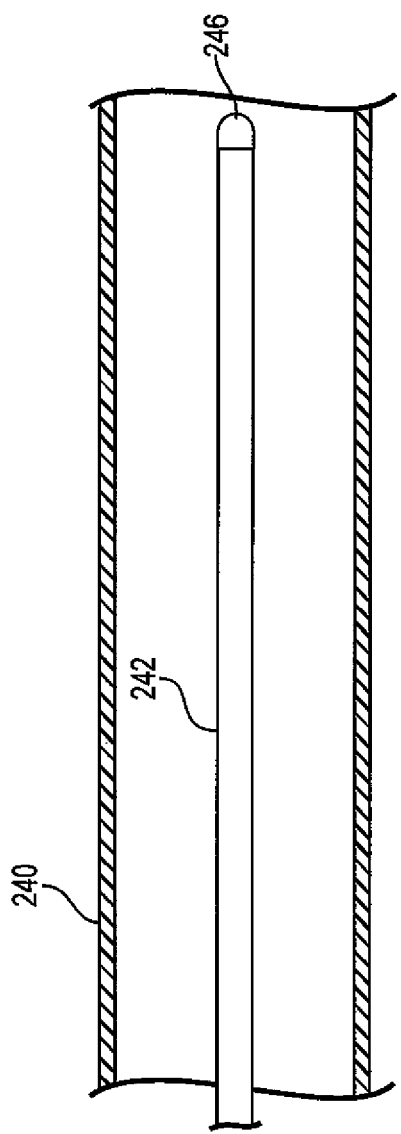
FIG. 17 is a front schematic view of an expansion member and probe of the invention.

FIG. 17 illustrates an expansion member 240, which may include features and structures of any of the expansion members or retractors described herein, and that includes a Doppler probe or transducer 246 at a distal end of a structure 242 that communicates with a proximal end of the expansion member 240 and a user. In a surgical procedure, the Doppler probe 246 can be useful to detect and avoid certain anatomical bodies, such as blood vessels and nearby nerves or other sensitive tissues. In this way, safe surgical locations can be discerned in order to avoid damaging those sensitive tissues. Alternately or additionally, an expansion member may be equipped at a distal end with infrared radiating or sensing functionality, for communication with a proximal end and a user, and for detecting and avoiding anatomical bodies such as blood vessels and arteries. Either or both of these features can be used in conjunction with any embodiments or features of devices, tools, implants, and methods described herein.

Retractors or expansion members of the invention can be structured to retract tissue of the small bowel, such as during a sacral colpopexy that places a component of an implant at a region of pelvic anatomy, or nearby. The structure, features, and functionality of the retractor can be as described herein, additionally with the distal end being structured to provide access to a sacrum while displacing tissue of a small bowel. The distal end feature can be in a retracted (i.e., collapsed or closed) state when positioned near the sacrum, beyond the peritoneum. Upon such placement, the distal end feature can be extended or opened, and additionally manipulated if necessary, to displace tissue including tissue of the small bowel.

Another method of controlling the position of a small bowel during a sacral colpopexy procedure involves placement of a component of an implant of the invention at a region of pelvic anatomy, or nearby. With such a method, the small bowel may be pressurized in a manner that is used in laparoscopic procedures. By placing a port inside the vagina, the small bowel can be pressurized to control the tissue and positioning of the tissue during placement of an implant at a region of sacral anatomy, for supporting vaginal tissue. The procedure could be performed through a single port, similar to a laparoscopic procedure.

Figure 18:
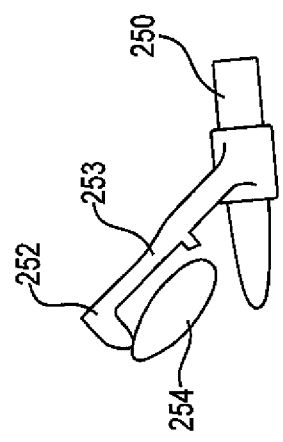
FIG. 18 is a front view of a retractor system of the invention.

FIG. 18 illustrates a system for retracting tissue during a sacral colpopexy procedure, including an introducer 250, as described herein, and a fixture 252 that includes a guide 253. The fixture 252 can fit externally to the patient, over the patient's skin and pubic bone 254, to be used as a guide for the expansion member. In particular, the external fixture 252 can be aligned with a centerline of the patient, externally, and can act to hold, manipulate, and guide a tool for use in a sacral colpopexy procedure, for example, by placing the tool or relevant structure of the tool on the same centerline, to align or position a distal feature of the tool at a desired location at or near a centerline of a sacrum. The tool may be a retractor, expansion member, speculum, etc., as described herein, or any other tool useful in a sacral colpopexy procedure.

FIGS. 19A-19C illustrate a peritoneum management system for use in a sacral colpopexy procedure (e.g., using a retractor or other tool or system as described herein). According to this system, a surface of a retractor 260 includes frictional structure 268 to engage a peritoneum (e.g., to create a barrier or seal at the interface), alternately or additionally to use the tool to grasp and manipulate the position of the peritoneum during the procedure. The retractor 260 further includes an outer curved surface 264 from which the frictional structure 268 extends and/or to which the frictional structure is attached, and a handle 262 extending outwardly from curved surface 264. The frictional structure 268 of retractor 260 can include small hooks, pins, channels, teeth, or other structure that can frictionally engage and grasp or hold tissue of the peritoneum 270. The frictional structure 268 may be fixed, or extendable and retractable by manipulation of an actuator at a proximal end of the tool. The frictional structure 268 may also extend from a series of hollow channels 266, as is illustrated in FIG. 19A, for example.

In use, frictional structure 268 at the distal end 272 of the tool 260 engages tissue of a peritoneum 270, wherein the peritoneum is severed as part of the procedure. The distal end continues to grasp the severed tissue of the peritoneum, to control the position of the severed tissue. The frictional surface can be located at the distal end tip of the tool and along a length, especially along a length of an opening, e.g., at edges of an opening that extends in a longitudinal direction along a length of the shaft of the tool, as is shown in the figures. For example, the distal end and a portion of a length of the tool may, during use, be located adjacent to a peritoneum. Edges or surfaces of these locations may include the described frictional surface features. The procedure may include making an incision of the peritoneum between the sacrum and the vaginal apex, and the frictional surfaces can be used to maintain the position of the peritoneum (adjacent to the tool) during the procedure.

Figure 20B:
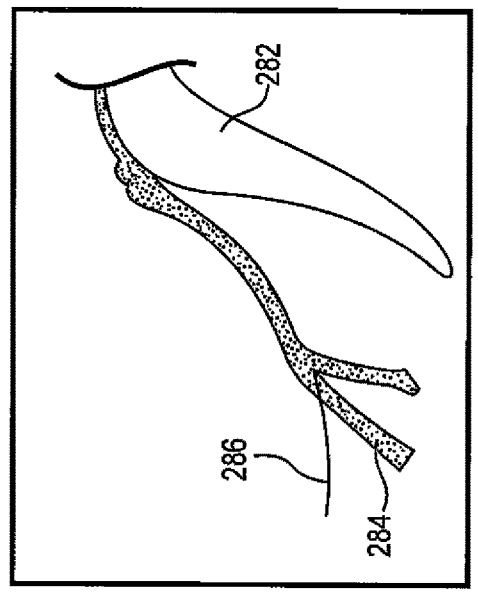
FIGS. 20A and 20B are perspective and front views of an implant placement relative to a patient's anatomy.
Figure 20A:
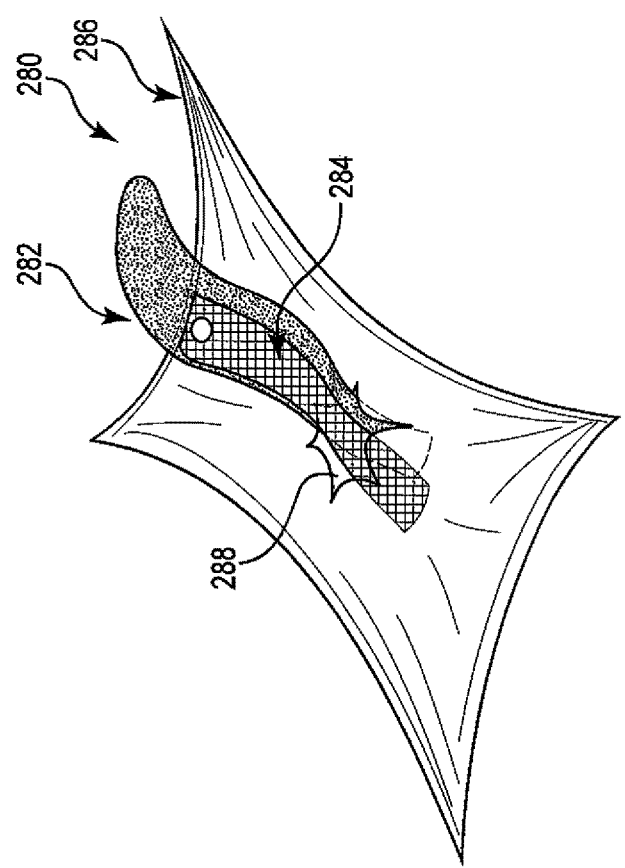
Figure 21A:
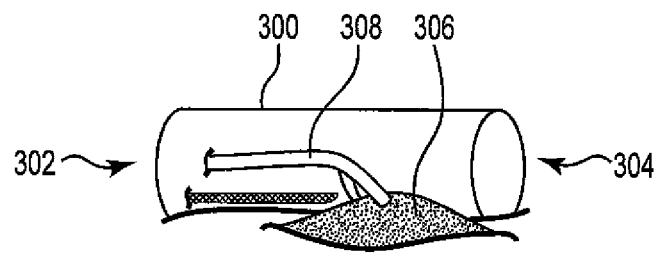
FIGS. 21A-21D are perspective views of a retractor and introducer being used to insert an implant.
Figure 21B:
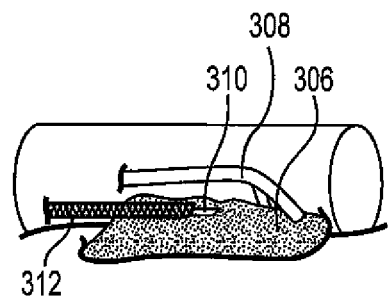
Figure 21C:
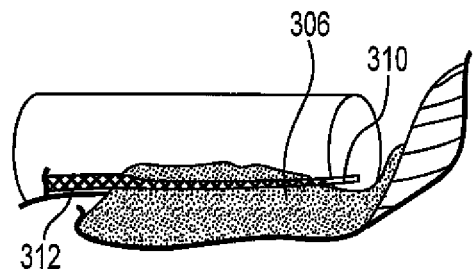
Figure 21D:
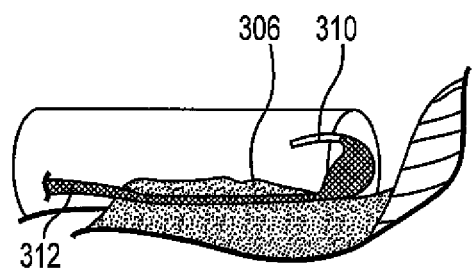

FIGS. 20A and 20B illustrate an exemplary sacral colpopexy procedure, as described, optionally using a tool, implant, system, or method as described, with placement of an implant 284 (e.g., mesh) at a location above the peritoneum 286. This may be facilitated by a perforation 288 of the perineum near the apex. Instead of placing an implant below the peritoneum, at least a portion of an implant is placed above (superior to) the peritoneum 286 (see FIG. 20B) and adjacent to the sacrum 282, and optionally attached to the peritoneum. This placement can reduce or eliminate the possibility of bowel obstruction and/or kinks. Fixation between the implant and peritoneum can be accomplished in any desired and useful manner, such as by suture, staple, hooks, pins, clips, Velcro, adhesive, etc.

Another embodiment of a sacral colpopexy method involves management of peritoneum tissue by use of a shaped implant or implant portion or component, such as a retractor described herein or elsewhere. In this embodiment, a shape of the implant conforms to the surface of a sacrum, so that when placed at the sacrum, the implant abuts against the sacrum and conforms to the shape of the sacrum. The peritoneum, adjacent to the sacrum, is thereby forced against the sacrum, between the sacrum and the implant, and is not able to become an obstruction to the surgeon. The implant may be rigid, semi-rigid, flexible, and may be prepared of mesh or a molded polymer. In somewhat more detail, the curved shape of the implant conforms to or hugs the sacral curve, e.g., to prevent bending, banding, binding, or obstruction of the small bowel. The placement of the implant and peritoneum forces the peritoneum to follow the sacral curvature and will prevent the bowel from becoming positioned beneath the implant, which could potentially cause a bowel obstruction.

Another sacral colpopexy method of the invention that involves management of peritoneum tissue involves using a retractor to manage an incision in the peritoneum. The retractor can be as described herein, e.g., two separate pieces that can be separated or moved in different directions relative to one another, optionally with frictional surfaces capable of engaging a peritoneum. For example, an expandable retractor can be placed so that the distal end can contact and engage a peritoneum, and to manage an incision made in the peritoneum by maintaining a separation between the two portions of a severed peritoneum. The peritoneum is severed generally to produce a right portion on a right side of the patient and a left portion on a left side of the patient, and each of the two sides of an expandable retractor can engage one portion, maintaining a separation between the right and left portions. Maintaining this separation also maintains the opening between the portions, at the cut, to improve access to the opening between the portions and the surgical site below the peritoneum, to facilitate placement of an implant below the peritoneum.

FIGS. 21A-21D illustrate an example of a method of using an expansion member or retractor 300 to gain access to a surgical site, to place a guide 310 (e.g., a guidewire) at a peritoneum 306, and to use the guide 310 to place a component of an implant. Accordingly, a method of the invention can involve placing a retractor (shown herein as retractor 300, but can be as described) to access a surgical site at a posterior pelvic region, such as at a region of sacral anatomy. Using a surgical tool such as a forceps 308, through the retractor 300, a surgeon grips the peritoneum 306 and inserts a guidewire 310 into the peritoneum 306. The guidewire 310 is advanced beneath the peritoneum 306 by a predetermined distance, then exits the peritoneum 306 at a more distal location. The guide 310 is deflected or re-directed to be pulled back out of the patient through the retractor 300, and an implant component 312 attached to the guide 310 is advanced into position underneath the peritoneum. The implant component can be useful to support tissue of a vaginal apex, or other tissue, e.g., in a sacrocolpopexy procedure.

Figure 22:
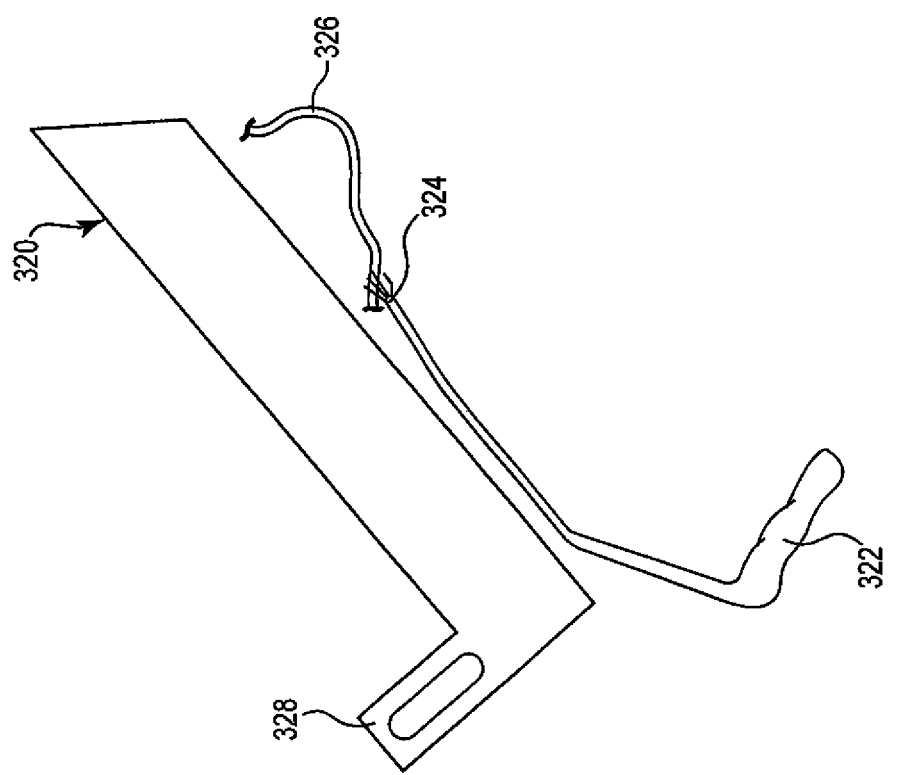
FIG. 22 is a side view of the use of a light with a retractor for an implantation procedure.

FIG. 22 illustrates an expansion member or retractor 320 as described herein, as it can be used with a light 324 located at a position along a shaft to illuminate a peritoneum 326, while the expansion member 320 is placed in a patient. For example, in a procedure that includes an apical vaginal incision and a posterior vaginal incision, the light 324 can be placed through the posterior incision, either connected to or separate from the expansion member. The light can be placed internally on the "external" side of the peritoneum, which is the side opposite of the location of the expansion member (i.e., inferior to or below the peritoneum). The light can be used to illuminate the peritoneum, shining through the peritoneum to identify any critical or sensitive structures before cutting or advancing a delivery tool. The procedure or tool may also include a feature for visualizing the peritoneum, e.g., electronically or through the expansion member. The expansion member can also include an opening (e.g., an elongate opening or slot) along a length of the expansion member shaft that allows access (including visual access) to the peritoneum.

FIG. 23 shows an example of an expansion member or retractor 340 that includes hooks 346 or another frictional structure capable of engaging and grasping a peritoneum, which is located at an edge or outer surface of the expansion member 340. These structures 340 are also discussed herein relative to FIGS. 19A-19C. With continued reference to FIG. 23, the retractor 340 includes three longitudinal sections 342 that are connected to each other by longitudinal hinges 344. It is understood that more or less than three sections 342 may be used, with a hinge 344 located between each adjacent pair of sections 342. In any case, the hinges 344 allow the retractor 340 to be expanded and contracted by folding the sections 342 relative to each other at the hinges 344 to thereby "open" or "close" the structure.

The hooks 346 are located at an edge of an elongate longitudinal opening 348 that is located between the distal ends of the first and last sections 342 of the retractor 340 on one side of and along a length of an expansion member. When the expansion member 340 is positioned with the distal end at a region of a sacrum, for example, one side (e.g., an inferior side or "bottom") of the shaft includes the length-wise opening or slot 348 that provides access to a peritoneum, located inferior to the shaft. Adjacent to that opening 348 (e.g., at a surface of the shaft, or at an edge of the opening) are the multiple hooks or other engagement structures 346 that are capable of engaging and grasping the peritoneum to allow the peritoneum to be controlled during a surgical procedure. For example, the hooks 346 may grasp the peritoneum for maintaining the position of the peritoneum as the peritoneum is severed along a centerline of the patient, to gain access to the underside of the peritoneum and a region of sacral anatomy. After the cut is made, hooks 346 on each side of the tool will maintain the position of the two portions of severed peritoneum.

Another embodiment of a sacral colpopexy procedure involves the use of peritoneum tissue, which is pulled together and used as a material to provide support for vaginal tissue. As a substitute for mesh, this method relies on the use of, e.g., multiple layers of peritoneum tissue that are pulled and secured together to create a material that will support the vaginal apex. Alternately, a small piece of mesh may be useful in combination with one or two layers of peritoneum, the combined mesh and peritoneum tissue being placed and attached to support tissue of a vaginal apex.

Figure 24B:
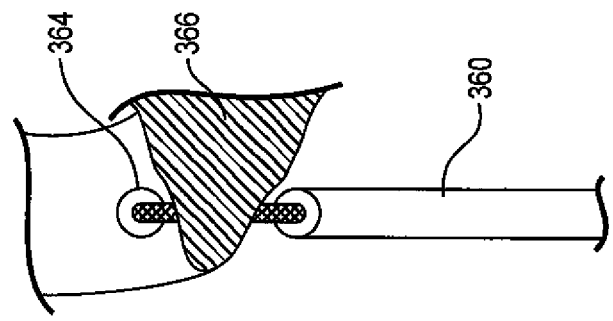
FIGS. 24A and 24B are schematic front views of a tool for use with an implant.
Figure 24A:
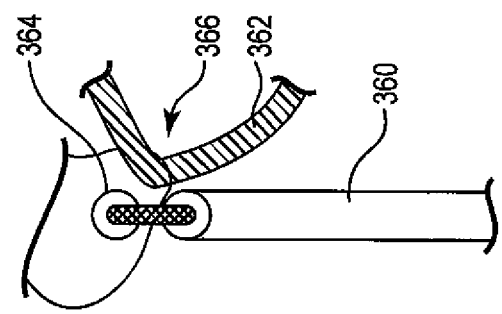

FIGS. 24A and 24B illustrate an embodiment of a method of attaching an implant to a component of sacral anatomy, using a tool 360, an implant 362 in the form of a tubular mesh, and an anchor 364. The implant 362 includes an anchor delivery mechanism for delivering a soft tissue anchor from the distal end, and frictional surfaces to engage tissue of a peritoneum 366, similar to that described herein relative to FIGS. 19A-19C and 23. In use, the tubular implant 362 is inserted to position the distal end at a region of a sacrum. The tubular implant 362 contains an elongate portion of an implant (e.g., mesh), having an anchor attached at the distal end. The soft tissue anchor attached to the implant is secured to a region of sacral anatomy. The frictional surfaces are used to engage the peritoneum 366. The tubular implant 362 is then rotated to pull the peritoneum 366 around it, thereby creating a tunnel of the peritoneal tissue. The peritoneum 366 can then be sutured or otherwise secured to itself to maintain the "tunnel" shape and opening around the implant (e.g., mesh). The tubular implant 362 can be withdrawn slightly, and the tool can again be used to grasp and rotate peritoneum tissue to form a tunnel, which is held together by another suture. These steps can be repeated to form a desired length of tunnel made of the peritoneal tissue, surrounding the implant. The tool can then be removed and the mesh implant remains behind within the peritoneal tunnel.

Figure 25B:
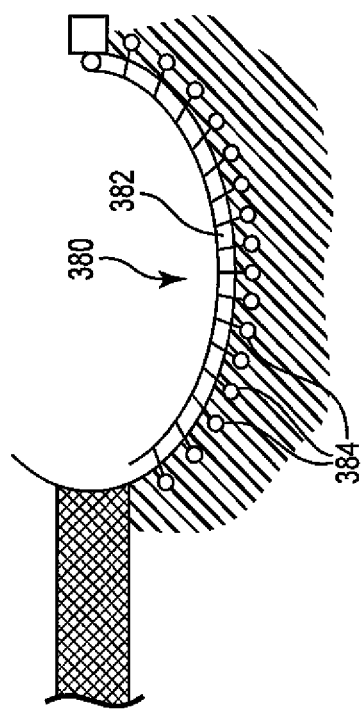
FIGS. 25A and 25B are bottom perspective and front views, respectively, of an implant of the invention.
Figure 25A:
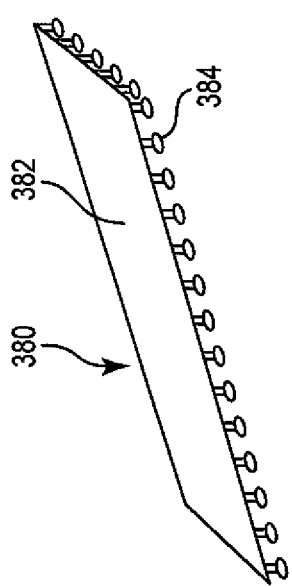

FIGS. 25A and 25B illustrate another example of a method and device for securing an implant material 380 directly to tissue of a peritoneum. The implant material 380 comprises a base material sheet 382 from which a frictional surface extends, which surface may comprise extension members 384 (e.g., clips, barbs, extensions, needles, hooks, "mushroom heads," Velcro-type (hook-and-loop) frictional structures, etc.). In order to engage this implant material 380 with a tissue, such as a peritoneum tissue, the implant can be positioned with its frictional surface in contact with the tissue, and then the material can be pressed toward and into the tissue until the frictional surface is sufficiently engaged with the tissue.

Figure 26:
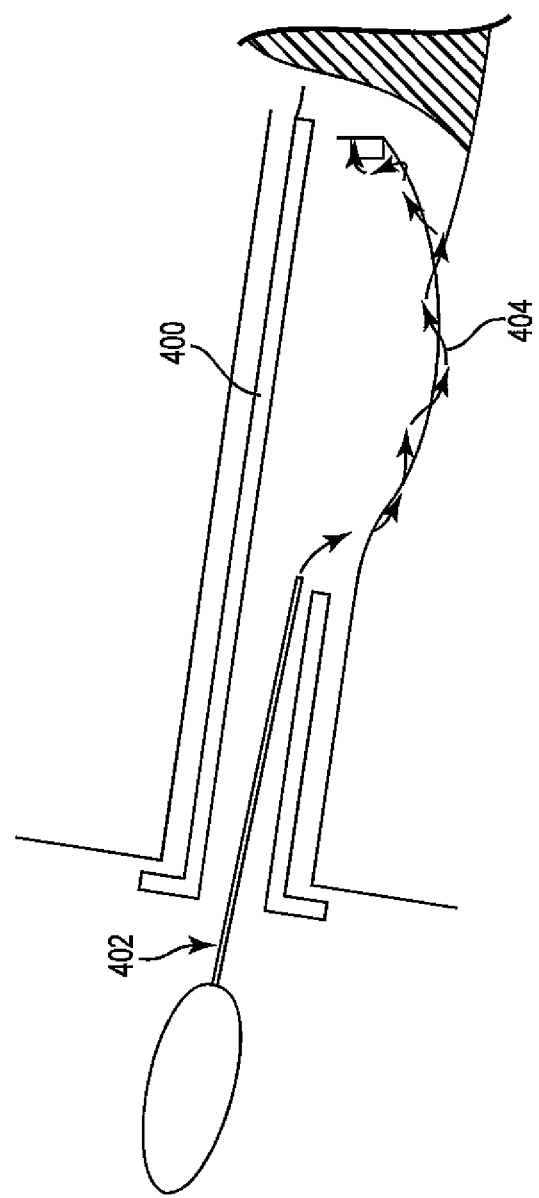
FIG. 26 is a schematic front view of an introducer being used to position an implant within a patient's anatomy.

FIG. 26 illustrates an example of a method, implant, and retractor that can be used to secure an implant at a region of a peritoneum and sacrum. The implant is passed, multiple times, through the peritoneum, from above to below, back to above, etc., "snaking" along a length of the peritoneum until it reaches the sacrum. An exemplary path that the implant can take is illustrated with arrows as path 404. Alternating the position of the implant on either side of the peritoneum mitigates, reduces, or eliminates, the need for additional fixating elements between the implant and the peritoneum, peritoneal closing devices, and potential banding that may occur. Friction between the implant and the peritoneum will provide securing force between the two. The implant may be placed as shown and described using a tool that can be passed alternately above, then below, the peritoneal tissue, e.g., "snaking" alternately above and below the tissue, then fixing the implant at a region of sacral anatomy such as an anterior longitudinal ligament. The tool can be withdrawn to leave the implant, placed as described.

FIGS. 27A and 27B illustrate another exemplary embodiment of a retractor 420 that includes a closing feature for closing an opening previously made in the peritoneum. As illustrated, the retractor 420 is a generally tubular shape and includes first and second sections 422, 424 attached at a longitudinal hinge 426 along the length of the retractor 420 so that the retractor 420 can open along its length on the side opposite the hinge (e.g., along a length of the retractor 420 that will be adjacent to a peritoneum when the retractor is installed in a sacral colpopexy procedure). Retractor 420 includes frictional structures for engaging tissue of a peritoneum, which are located along the length of the retractor adjacent to the peritoneum when installed.

In use, the retractor 420 can be used to close the surgical opening in the peritoneum. After a surgical procedure, the retractor 420 is opened along the hinge 426, and the frictional structures located longitudinally on opposite edges of the opening contact opposite sides of a severed peritoneum. The retractor 420 is then closed, squeezing the opposite sides of severed peritoneum between the edges, which may include catching the opposite sides of the peritoneum with the clips to hold the sides together for healing.

FIG. 28 illustrates another embodiment of a retractor 440 that includes frictional structures 442 (e.g., pins, wires, etc.) on the inside of the retractor 440 for engaging tissue of a peritoneum on exterior surface of the retractor. In this way, after the peritoneum is cut open, the peritoneum can be pushed to either side and stick to the walls of the retractor 440. In one embodiment, the frictional structures 442 can be angled upwardly so that the peritoneum does not slide off during mesh placement.

The methods, tools, expansion members, and implants described can be used in conjunction with any type of anchor for securing an implant to tissue, such as at a region of sacral anatomy using a soft tissue anchor. FIGS. 29A-29C and 30A-30B show a system 450 for securing a pincher-type soft tissue anchor to soft tissue, e.g., a peritoneum, a ligament, muscle, etc., optionally at a region of sacral anatomy. The assembly includes a pincher anchor 452, a ring 454, and an insertion tool 456. The ring and insertion tool are used together to position the pincher anchor 452 at a location of soft tissue, and to close the jaws of the pincher anchor 452 to grip into and become secured to the soft tissue, leaving behind the pincher anchor 452 and the ring 454 secured to the soft tissue, for supporting an implant.

Figure 30A:
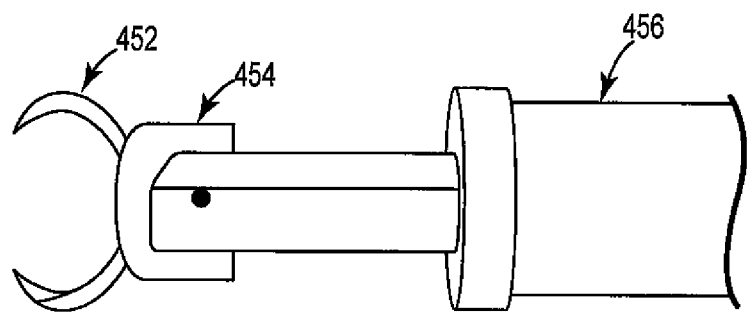
FIGS. 30A and 30B are perspective views of a tool being used with the anchor and ring of FIGS. 29A-29C.

FIG. 30A illustrates the elongate tool 456 with a shaft) and the pincher-anchor and ring (collar) at the distal end of the tool 456 with jaws open. In use, the target soft tissue can be identified and the assembly can be positioned adjacent to soft tissue with jaws open, as illustrated in FIG. 30A. Next, the outer ring is slid distally relative to the jaws, causing the jaws to pivot together and close. To close the jaws, the ring may be pushed distally relative to the shaft, the pincher-anchor can be pulled proximally relative to the shaft, or a combination of these movement may be used.

Figure 30B:
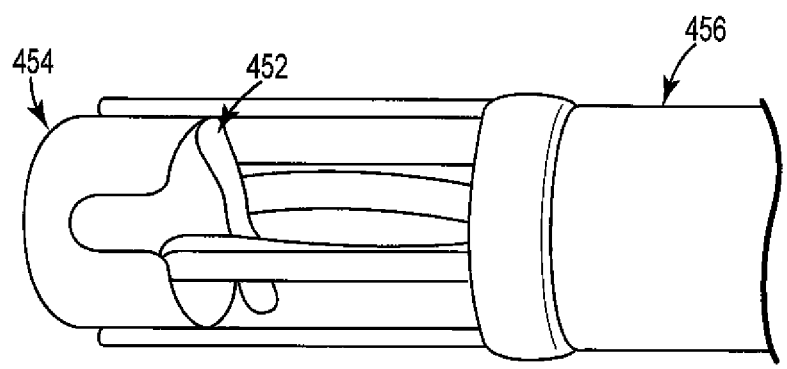

After the jaws are closed on the soft tissue, the tool 456 can be disengaged and withdrawn, leaving the pincher anchor and ring (collar) 456 in place secured to soft tissue. Any release mechanism can be useful. As illustrated, an actuator at the delivery tool handle can be moved (e.g., rotated) to release an engagement between the ring and delivery tool bars by spreading the bars apart, as shown in FIG. 30B. The inner supports can be rotated to align with channels in the ring, the tool can be withdrawn.

Extending between the handle and the distal end is an elongate shaft section, which is connected to the moveable retractor surfaces through hinges. A removable retractor section can be engaged with the shaft to produce an inner space along a length of the retractor, which can be a working space of the retractor to allow access to a surgical site. The removable retractor section can include an opening (e.g., slot) at the distal to allow lateral access to a surgical site.

In cross section, the shaft includes two abutments along a length of the shaft; each abutment is capable of engaging a structure of the removable section to allow a removable engagement between the shaft and the removable section. For example, as illustrated, two opposing longitudinal edges or lips (continuous or interrupted), each located along a length of the removable section, can be fit behind the to abutments to place the removable section of in a working engagement with the shaft. In cross-section the removable section is semi-circular, and the spine is curved, such that when engaged the two sections of the expansion member produce a curved space.

The moveable retractor surfaces at the distal end can function to retract tissue at a surgical location by moving laterally upon rotating or pivoting about the hinges. The moveable retractor surfaces can be located along a length of the shaft at the distal end, optionally not extending along the entire length of the shaft but only along a partial length of the shaft at the distal end. The moveable retractor surfaces can be of any cross-sectional shape or form, such as curved or straight (flat).

Expansion member devices as described and illustrated herein, sometimes referred to interchangeably as "tubes," "speculums," "retractors," etc., can be used and useful according to methods of inserting the device into a surgical incision, and moving, retracting, displacing, or expanding tissue to provide access to desired anatomy. For performing certain surgical procedures, a tube or retractor can be placed in a non-expanded, collapsed state. The device or a related structure can then be expanded while in place to create access to desired anatomy such as the posterior of a pelvic region, e.g., to gain access to a region of sacral anatomy; to create a workspace between a vaginal introitus and a region of a sacrum, such as an anterior longitudinal ligament, sacral promontory, or peritoneum. A surgeon can perform a surgical procedure by use of the access, which provides working space to pelvic anatomy such as the sacrum and surrounding tissue as described.

Methods of utilizing devices of the invention can optionally also involve a tool, multi-functional tool, implant, adjustable implant, anchor (soft tissue anchor or bone anchor), or other device or method described herein. Optional features and structures (e.g., fiber optics) to allow viewing or illumination, or any other functionality at the distal end can be incorporated into any of these types of devices. For example, if a structural component of the device is made of a plastic or polymeric light-conductive material, light can be transmitted through that material from a proximal end to a distal end at the surgical site. Alternately, a fiber optic cable can be incorporated into a length of the device, extending from a proximal to or toward a distal end, to allow light to be transmitted from the proximal end to the distal end, or to allow images to be transmitted from the distal end to the proximal end. Light could alternately be generated and shone from the distal end.

The implants, their various components, structures, features, materials and methods may have a number of suitable configurations as shown and described in the previously-incorporated references, or as described herein. Various methods and tools for introducing, deploying, anchoring and manipulating implants to treat incontinence, prolapse, or another pelvic condition, as disclosed in the previously-incorporated references are envisioned for use with the present invention as well as those methods and tools identified and described herein.

Also according to embodiments of the methods, implants, tools, and devices described herein, any of the described tools can be used for placing any desired pelvic implant in a male or a female patient, and for any of a large variety of conditions, such as a pelvic condition. The implant can include any structural features useful for such treatment, including any desired size, shape, and optional features such as adjustability and anchoring systems. Any of these features may be previously known, future developed, described herein, or described in documents incorporated herein, for any particular implant and method. For example, some figures and discussions include examples of features of "anchors" (e.g., soft tissue or bone anchors, as these terms are generically and inclusively used) that can be useful according to the methods of placing a surgical implant. An implant that includes or is otherwise secured by any of the anchors described can be useful to treat a pelvic condition in a male or a female patient.

Various devices and methods described herein are advantageous because they facilitate reduction of total procedural time if the patient needs a urinary sling, levator floor support, high apical support (fixation to the sacrum), and anterior or posterior prolapse by combining multiple products into one. The pelvic floor support reduces the long term prolapse recurrence as well as improve the patient's sexual function with the high apical support due to the sacral fixation. Moreover, the various tools and methods allow a physician to use a transvaginal approach, an abdominal approach, or a laparoscopic approach to achieve a similar tension as what is currently only achievable for sacral colpopexy procedures.

The various systems, apparatus, and methods detailed herein are envisioned for use with many known implant and repair systems (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261, WO 2007/097994, WO 2007/149348, and U.S. Patent Publication Nos. 2002/151762, 2010-0174134, 2010-0298630, and 2002/147382.

Accordingly, the above-identified disclosures are fully incorporated herein by reference in their entirety.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

The invention claimed is:

1. A retractor assembly for retracting pelvic tissue, the assembly comprising:
    an introducer including:
        an open proximal end having a first cross-sectional dimension;
        a closed distal end having a second cross-sectional dimension and including a distal tip;
        an inner opening extending along a length of the introducer through the open proximal end to the closed distal end of the introducer; and
        an outer shell defining the inner opening, the outer shell including a first section and a second section, the first section being removably attached to the second section along one seam that continuously extends longitudinally from the open proximal end on one lateral side of the introducer, transversely across the distal tip, to the open proximal end of the other lateral side of the introducer; and
    a retractor including:
        an open proximal end having a first cross-sectional dimension;
        a distal end having a second cross-sectional dimension; and
        a body defining an inner opening and having a first outer periphery that is smaller than the inner opening of the introducer along at least a portion of a length of the retractor, such that at least a portion of the length of the retractor is insertable into the inner opening of the introducer at the open proximal end of the introducer,
    wherein the first cross-sectional dimension of the proximal end of the introducer is substantially larger than the second cross-sectional dimension of the distal end of the introducer and the first cross-sectional dimension of the proximal end of the retractor is substantially larger than the second cross-sectional dimension of the distal end of the retractor,
    wherein the retractor is expandable such that the body attains a second outer periphery that is larger than the inner opening of the introducer, the retractor is expandable such that the proximal end of the retractor has a third cross-sectional dimension and the distal end of the retractor has a fourth cross-sectional dimension, the third cross-sectional dimension of the proximal end of the retractor being substantially larger than the fourth cross-sectional dimension of the distal end of the retractor.

2. The retractor assembly of claim 1, wherein each of the first and second sections of the outer shell comprises approximately one half of the outer shell of the introducer.

3. The retractor assembly of claim 1, wherein one of the first and second sections of the outer shell comprises more than one half of the outer shell of the introducer.

4. The retractor assembly of claim 1, wherein at least a portion of the introducer is transparent or translucent.

5. The retractor assembly of claim 1, further comprising at least one handle extending outwardly from the body adjacent to the proximal end of the retractor.

6. The retractor assembly of claim 5, wherein the at least one handle is foldable relative to the body of the retractor.

7. The retractor assembly of claim 1, wherein the outer shell of the introducer is tapered from the open proximal end to the closed distal end such that a size of the inner opening becomes smaller along the length of the introducer.

8. The retractor assembly of claim 1, wherein the outer shell of the introducer is tapered along its length from a first outer periphery at the open proximal end down to a second outer periphery at the closed distal end.

9. The retractor assembly of claim 1, wherein the closed distal end of the introducer is completely closed.

10. The retractor assembly of claim 1, wherein the retractor includes a first handle member extending from the body of the retractor at a first location, and a second handle member extending from the body of the retractor at a second location, wherein the first handle member and the second handle member are configured to move relative to the body of the retractor.

* * * * *